(12) United States Patent
Ohmori et al.

(10) Patent No.: US 8,927,157 B2
(45) Date of Patent: Jan. 6, 2015

(54) CONDENSED POLYCYCLIC AROMATIC COMPOUND, PRODUCTION PROCESS OF SAME, AND POSITIVE ELECTRODE ACTIVE MATERIAL FOR LITHIUM ION SECONDARY BATTERY CONTAINING SAME

(75) Inventors: Osamu Ohmori, Kariya (JP); Akiko Shima, Kariya (JP); Hitotoshi Murase, Kariya (JP); Masataka Nakanishi, Kariya (JP); Junichi Niwa, Kariya (JP); Kimihisa Yamamoto, Yokohama (JP)

(73) Assignees: Kabushiki Kaisha Toyota Jidoshokki, Aichi (JP); Keio University, Tokyo (JP)

( * ) Notice: Subject to any disclaimer, the term of this patent is extended or adjusted under 35 U.S.C. 154(b) by 57 days.

(21) Appl. No.: 13/701,544

(22) PCT Filed: May 26, 2011

(86) PCT No.: PCT/JP2011/062641
§ 371 (c)(1),
(2), (4) Date: Dec. 3, 2012

(87) PCT Pub. No.: WO2011/152476
PCT Pub. Date: Dec. 8, 2011

(65) Prior Publication Data
US 2013/0078514 A1 Mar. 28, 2013

(30) Foreign Application Priority Data
Jun. 1, 2010 (JP) ................. 2010-126029

(51) Int. Cl.
*H01M 4/60* (2006.01)
*C07C 251/22* (2006.01)
*C07C 249/02* (2006.01)
*H01M 10/052* (2010.01)
*C07B 61/00* (2006.01)
*H01M 4/02* (2006.01)

(52) U.S. Cl.
CPC ............. *H01M 4/606* (2013.01); *C07C 251/22* (2013.01); *H01M 4/60* (2013.01); *H01M 4/608* (2013.01); *H01M 10/052* (2013.01); *H01M 2004/028* (2013.01); *Y02E 60/122* (2013.01)
USPC ......................................... 429/303; 564/270

(58) Field of Classification Search
USPC ............ 429/300, 303; 252/510, 511; 564/270
See application file for complete search history.

(56) References Cited

U.S. PATENT DOCUMENTS 5,258,140 A    11/1993   Chetcuti
5,378,744 A    1/1995   Chetcuti (Continued)

FOREIGN PATENT DOCUMENTS

JP    05-247257 A    9/1993
JP    05-310675 A    11/1993

(Continued)

OTHER PUBLICATIONS

S.F. Rak et al., "Mixed Valence in Conjugated Anion Radicals Solution and Solid State Studies", Synthetic Metals, Compound 3, May 24, 1991, pp. 2365-2375, vol. 42, No. 3.

(Continued)

*Primary Examiner* — Gregg Cantelmo
(74) *Attorney, Agent, or Firm* — Sughrue Mion, PLLC

(57) ABSTRACT

Provided is a condensed polycyclic aromatic compound, having lithium ion responsivity and is suitable for lithium ion secondary battery applications, a production process thereof, a positive electrode active material containing that condensed polycyclic aromatic compound, and a positive electrode for a lithium ion secondary battery provided therewith, and further provided is a lithium ion secondary battery, having high capacity and cycling adaptability, that has the positive electrode as a constituent thereof. The condensed polycyclic aromatic compound has at least four imino groups in a molecule thereof.

19 Claims, 9 Drawing Sheets

(56) References Cited

U.S. PATENT DOCUMENTS

| | | | |
|---|---|---|---|
| 5,393,606 | A | 2/1995 | Chetcuti |
| 6,465,116 | B1 | 10/2002 | Ishikawa et al. |
| 2008/0207864 | A1 | 8/2008 | Nakagawa et al. |

FOREIGN PATENT DOCUMENTS

| | | |
|---|---|---|
| JP | 06-100522 A | 4/1994 |
| JP | 11-354277 A | 12/1999 |
| JP | 2005-263721 A | 9/2005 |

OTHER PUBLICATIONS

International Search Report of PCT/JP2011/062641 dated Aug. 23, 2011.

Hart et al., "Synthesis of Heptiptycenes with Face-to-Face Arene Rings via a 2,3:6,7-Anthradiyne Equivalent", Journal of Organic Chemistry, vol. 48, No. 23, 1983, pp. 4357-4360.

Rak et al., "Mixed-Valence, Conjugated Quinone and Imide Anion Radicals. An ESR Investigation", Journal of American Chemical Society, vol. 114, No. 4, 1992, pp. 1388-1394.

Ashton et al., "Molecular LEGO. 1. Substrate-Directed Synthesis via Stereoregular Diels-Alder Oligomerizations", Journal of American Chemical Society, vol. 114, No. 16, 1992, pp. 6330-6341.

Tapia et al., "Synthesis of Indazol-4, 7-dione Derivatives as Potential Trypanocidal Agents", Journal of Heterocyclic Chemistry, vol. 39, Sep.-Oct. 2002, pp. 1093-1096.

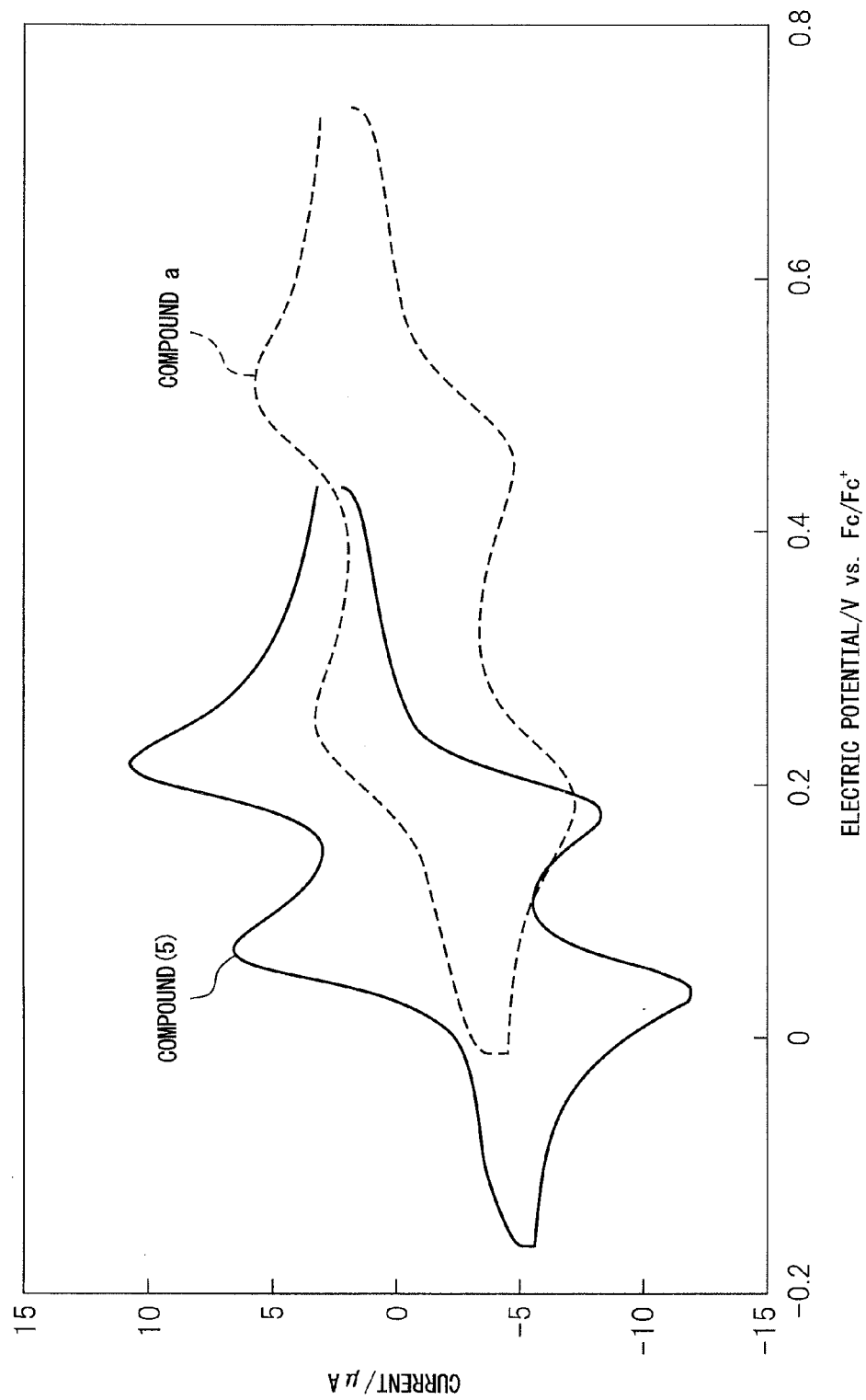

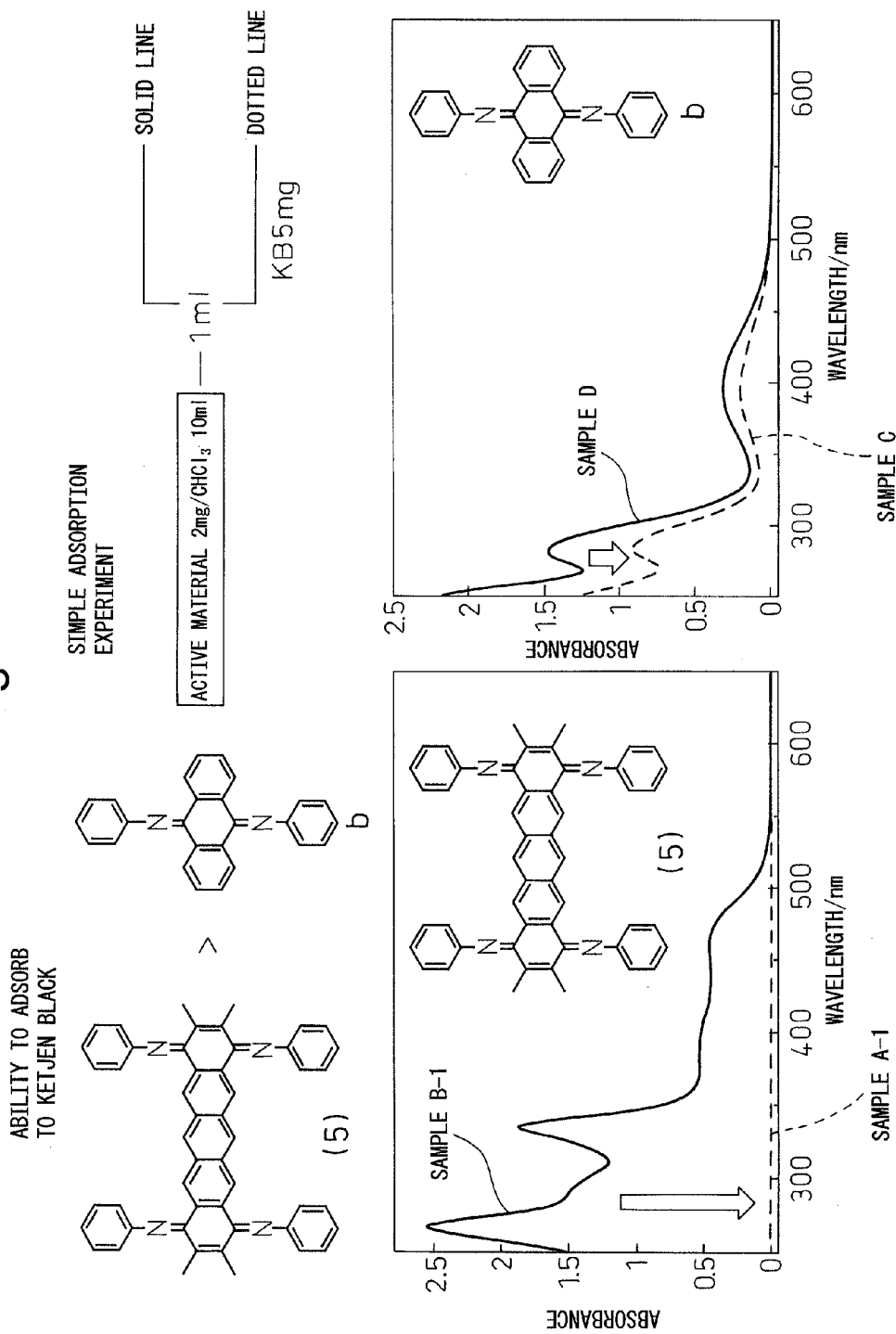

CONDENSED POLYCYCLIC AROMATIC COMPOUND, PRODUCTION PROCESS OF SAME, AND POSITIVE ELECTRODE ACTIVE MATERIAL FOR LITHIUM ION SECONDARY BATTERY CONTAINING SAME

CROSS REFERENCE TO RELATED APPLICATIONS

This application is a National Stage of International Application No. PCT/JP2011/062641 filed May 26, 2011, claiming priority based on Japanese Patent Application No. 2010-126029 filed Jun. 1, 2010, the contents of all of which are incorporated herein by reference in their entirety.

TECHNICAL FIELD

The present invention relates to condensed polycyclic aromatic compound, a production process thereof, and a positive electrode active material for a lithium ion secondary battery that contains the condensed polycyclic aromatic compound, and further relates to a positive electrode provided with the positive electrode active material and a lithium ion secondary battery having the positive electrode as a constituent thereof.

BACKGROUND ART

Accompanying the reduced size and the increasingly advanced functions of cell phones and other electronic devices, there is a growing demand for the lithium ion secondary batteries used in these devices to have lighter weight, increased capacity and longer life (cycling adaptability). However, since oxides of cobalt and manganese having high specific gravity are used for the positive electrode active materials of lithium ion secondary batteries primarily used at present, the lithium ion secondary batteries are heavy. Therefore, although reducing the ratio of positive electrode active material in the entire lithium ion secondary battery can be considered for reducing the total weight of lithium ion secondary batteries, in this case, there is a high likelihood that capacity and lifetime (cycling adaptability) cannot be expected to improve even though a reduction in weight can be achieved.

Extensive studies have been conducted in recent years on whether or not organic compounds composed of light elements and the like can be applied for use as positive electrode active materials. Pi-conjugated, electrically conductive polymers are particularly promising for use as positive electrode active materials. For example, Patent Document 1 describes a secondary battery that uses a novel polyaniline derivative compound of an electrically conductive polymer enabling one-step, two-electron transfer, and the use of a protonated form of the compound in a positive electrode. According to Patent Document 1, since an electrode material using the novel polyaniline derivative compound has high energy density, the use of that electrode material as a positive electrode is described as being useful in a secondary battery that uses a zinc plate for the negative electrode and an aqueous zinc sulfate solution for the electrolyte solution. However, in terms of increasing capacity and lengthening lifetime (cycling adaptability), further improvements are being sought, and extensive studies are currently being conducted as to whether or not novel organic compounds and the like can be applied to positive electrode active materials for lithium ion secondary batteries.

Patent Document 2 describes a production process for generating pentacene by irradiating an oxygen adduct of a pentacene derivative with ultraviolet light. According to Patent Document 2, this production process is described as being highly superior in terms of being environmentally clean since it does not generate harmful gas and can be easily recycled, while at the same time enabling optical patterning, thereby reducing the burden on the environment and natural resources.

PRIOR ART DOCUMENTS

Patent Documents

Patent Document 1: Japanese Unexamined Patent Publication No. 2005-2278
Patent Document 2: Japanese Unexamined Patent Publication No. 2008-285442

SUMMARY OF THE INVENTION

Problems to be Solved by the Invention

An object of the present invention is to provide a condensed polycyclic aromatic compound having superior lithium ion responsivity and is suitable for lithium ion secondary battery applications, a production process thereof, a positive electrode active material containing that condensed polycyclic aromatic compound, and a positive electrode of a lithium ion secondary battery provided therewith. Moreover, an object of the present invention is to provide a lithium ion secondary battery having high capacity and superior cycling adaptability that has that positive electrode as a constituent thereof.

Means for Solving the Problems

As a result of extensive studies to achieve the aforementioned objects, the inventors of the present invention found that a condensed polycyclic aromatic compound having at least four imino groups in a molecule thereof demonstrates multi-electron transfer and has superior lithium ion responsivity, and that the condensed polycyclic aromatic compound demonstrates high adhesiveness with electrode materials and is preferable for application to lithium ion secondary batteries, thereby leading to completion of the present invention.

Specific means for achieving the aforementioned objects are as described below.

(1) A condensed polycyclic aromatic compound having at least four imino groups in a molecule thereof.
(2) The condensed polycyclic aromatic compound described in (1), which is represented by the following general formula (1):

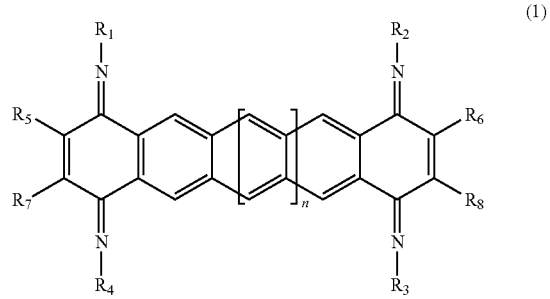

(wherein, $R_1$, $R_2$, $R_3$, $R_4$, $R_5$, $R_6$, $R_7$ and $R_8$ respectively and independently represent a hydrogen atom, substituted or unsubstituted aliphatic hydrocarbon group or substituted or unsubstituted aromatic hydrocarbon group, and n represents an integer of 1 to 10).

(3) The condensed polycyclic aromatic compound described in (1), which is represented by the following general formula (2):

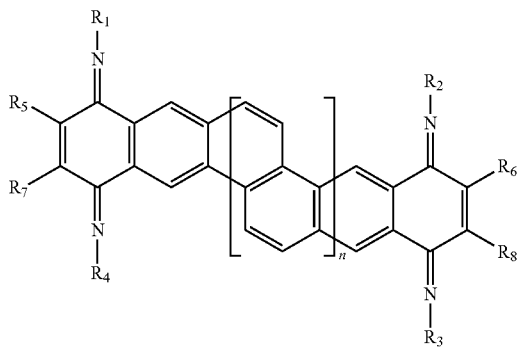

(2)

(wherein, $R_1$, $R_2$, $R_3$, $R_4$, $R_5$, $R_6$, $R_7$ and $R_8$ respectively and independently represent a hydrogen atom, substituted or unsubstituted aliphatic hydrocarbon group or substituted or unsubstituted aromatic hydrocarbon group, and n represents an integer of 1 to 10).

(4) A production process of the condensed polycyclic aromatic compound described in (1), comprising reacting a compound having at least four oxo groups in a molecule thereof with an aniline-based compound in the presence of titanium tetrachloride and base.

(5) A production process of the condensed polycyclic aromatic compound described in (2), comprising reacting a compound represented by the following general formula (3) with an aniline-based compound in the presence of titanium tetrachloride and base:

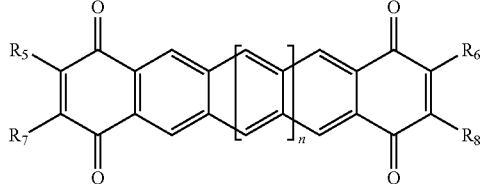

(3)

(wherein, $R_5$, $R_6$, $R_7$ and $R_8$ are respectively the same as defined for $R_5$, $R_6$, $R_7$ and $R_8$ in general formula (1), and n represents an integer of 1 to 10).

(6) A production process of the condensed polycyclic aromatic compound described in (3), comprising reacting a compound represented by the following general formula (4) with an aniline-based compound in the presence of titanium tetrachloride and base:

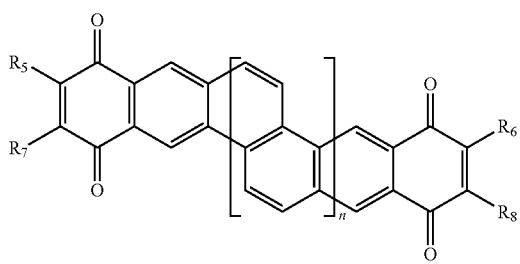

(4)

(wherein, $R_5$, $R_6$, $R_7$ and $R_8$ are respectively the same as defined for $R_5$, $R_6$, $R_7$ and $R_8$ in general formula (2), and n represents an integer of 1 to 10).

(7) A positive electrode active material for a lithium ion secondary battery containing the condensed polycyclic aromatic compound described in any of (1) to (3).

(8) A positive electrode for a lithium ion secondary battery, wherein the positive electrode active material described in (7) is provided at least on the surface of a current collector.

(9) A lithium ion secondary battery comprising at least a positive electrode, a negative electrode and an electrolyte solution as constituents thereof, wherein the positive electrode is the positive electrode described in (8).

Effects of the Invention

According to the present invention, a condensed polycyclic aromatic compound, having superior lithium ion responsivity and is suitable for lithium ion secondary battery applications, a production process thereof, a positive electrode active material containing the condensed polycyclic aromatic compound, a positive electrode provided therewith, and a lithium ion secondary battery having the positive electrode as a constituent thereof, are provided.

BRIEF DESCRIPTION OF THE DRAWINGS

FIG. 2-1 is a graph showing the results of evaluating multi-electron transfer carried out in Example 3 and Comparative Example 1.

FIG. 2-2 is a graph showing the results of evaluating multi-electron transfer carried out in Example 3.

FIG. 7-1 is a drawing showing the results of an adsorption test carried out on a conductive assistant (Ketjen black) in Example 5 and Comparative Example 3.

FIG. 7-2 is a drawing showing the results of an adsorption test carried out on a conductive assistant (Ketjen black) in Example 5 and Comparative Example 3.

FIG. 7-3 is a drawing showing the results of an adsorption test carried out on a conductive assistant (Ketjen black) in Example 5 and Comparative Example 3.

EMBODIMENTS OF THE INVENTION

Figure 1:
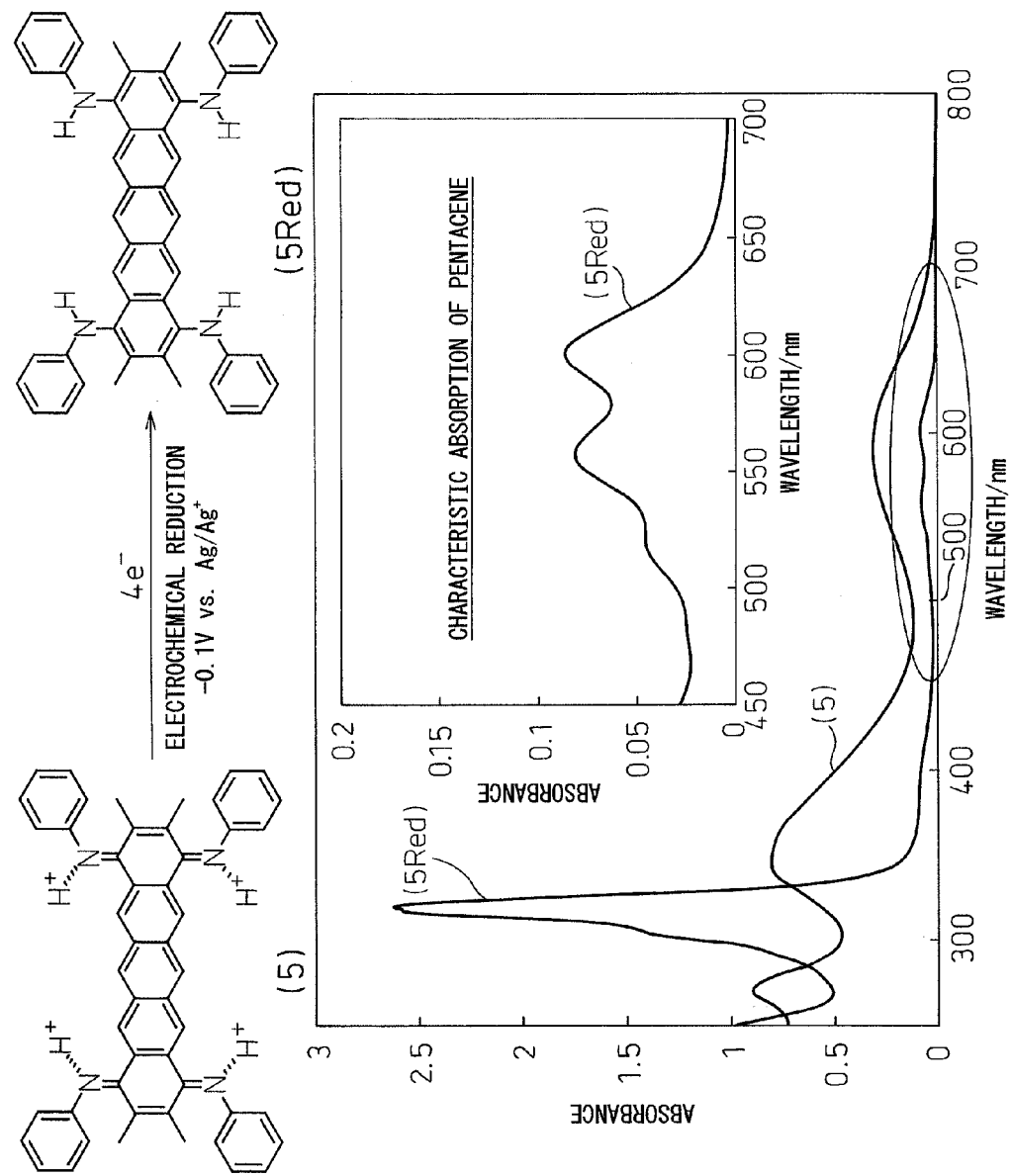
FIG. 1 is a drawing showing the visible-ultraviolet spectra of a condensed polycyclic aromatic compound (5Red) formed by an electrochemical reduction reaction carried out in Example 2 and a condensed polycyclic aromatic compound (5) prior to an electrochemical reduction reaction.

The following provides a more detailed explanation of the present invention.
(1) Condensed Polycyclic Aromatic Compound
The condensed polycyclic aromatic compound according to the present invention is characterized by having at least four imino groups in a molecule thereof. Although there are no particular limitations on the condensed polycyclic aromatic compound according to the present invention provided it has at least four imino groups, it is preferably a compound represented by the following general formula (5).

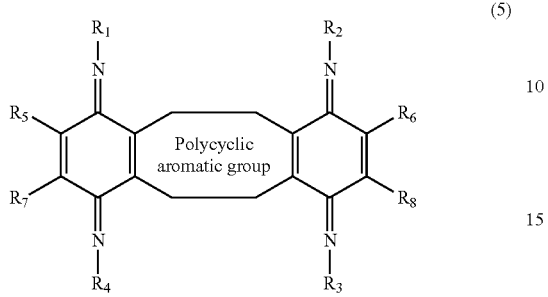

(5)

In general formula (5), $R_1$, $R_2$, $R_3$, $R_4$, $R_5$, $R_6$, $R_7$ and $R_8$ respectively and independently represent a hydrogen atom, substituted or unsubstituted aliphatic hydrocarbon group or substituted or unsubstituted aromatic hydrocarbon group.

There are no particular limitations on $R_1$, $R_2$, $R_3$, $R_4$, $R_5$, $R_6$, $R_7$ and $R_8$ provided they are electron donating groups, and examples thereof respectively and independently include an alkyl group such as a methyl group, ethyl group, n-propyl group, isopropyl group, sec-butyl group, isobutyl group or tert-butyl group, a cycloalkyl group such as a cyclopentyl group or cyclohexyl group, an alkenyl group such as a vinyl group or allyl group, and an aryl group such as a phenyl group, tolyl group or naphthyl group.

There are no particular limitations on substituents of $R_1$, $R_2$, $R_3$, $R_4$, $R_5$, $R_6$, $R_7$ and $R_8$ when they are substituted with substituents, and examples thereof include aryl groups such as a phenyl group, tolyl group or naphthyl group, and alkoxy groups such as a methoxy group, ethoxy group, propoxy group, isopropoxy group, butoxy group, sec-butoxy group or tert-butoxy group.

$R_1$ to $R_4$ are more preferably aryl groups and even more preferably phenyl groups. $R_5$ to $R_8$ are more preferably alkyl groups and even more preferably methyl groups.

The polycyclic aromatic group in general formula (5) represents a substituted or unsubstituted polycyclic aromatic group. There are no particular limitations on substituents of a substituted polycyclic aromatic group when it is substituted with substituents, and examples include alkyl groups such as a methyl group, ethyl group, n-propyl group, isopropyl group, sec-butyl group, isobutyl group or tert-butyl group, cycloalkyl groups such as a cyclopentyl group or cyclohexyl group, alkenyl groups such as a vinyl group or allyl group, and aryl groups such as a phenyl group, tolyl group or naphthyl group.

Preferable examples of unsubstituted polycyclic aromatic groups include, but are not limited to, the groups indicated below.

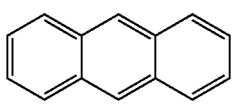

$Y_1$

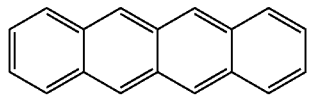

$Y_2$

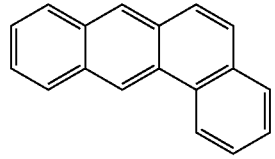

$Y_3$

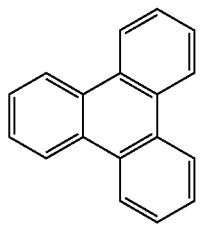

$Y_4$

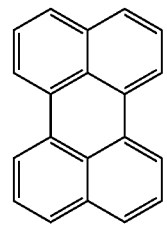

$Y_5$

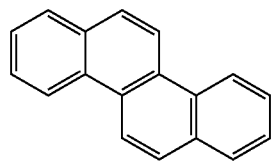

$Y_6$

In addition, the condensed polycyclic aromatic compound according to the present invention is preferably a compound represented by the following general formula (1).

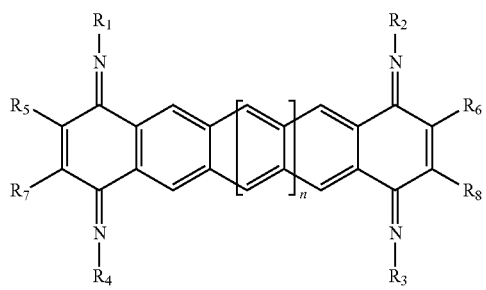

(1)

In general formula (1), $R_1$, $R_2$, $R_3$, $R_4$, $R_5$, $R_6$, $R_7$ and $R_8$ respectively and independently represent a hydrogen atom, substituted or unsubstituted aliphatic hydrocarbon group or substituted or unsubstituted aromatic hydrocarbon group, and n represents an integer of 1 to 10.

There are no particular limitations on $R_1$, $R_2$, $R_3$, $R_4$, $R_5$, $R_6$, $R_7$ and $R_8$ provided they are electron donating groups, and examples thereof respectively and independently include an alkyl group such as a methyl group, ethyl group, n-propyl group, isopropyl group, sec-butyl group, isobutyl group or tert-butyl group, a cycloalkyl group such as a cyclopentyl group or cyclohexyl group, an alkenyl group such as a vinyl group or allyl group, and an aryl group such as a phenyl group, tolyl group or naphthyl group.

There are no particular limitations on substituents of $R_1$, $R_2$, $R_3$, $R_4$, $R_5$, $R_6$, $R_7$ and $R_8$ when they are substituted with substituents, and examples thereof include aryl groups such as a phenyl group, tolyl group or naphthyl group, and alkoxy groups such as a methoxy group, ethoxy group, propoxy group, isopropoxy group, butoxy group, sec-butoxy group or tert-butoxy group.

$R_1$ to $R_4$ are more preferably aryl groups and even more preferably phenyl groups. $R_5$ to $R_8$ are more preferably alkyl groups and even more preferably methyl groups.

n is an integer of 1 to 10 that represents the degree of polymerization. n is preferably an integer of 5 or less.

Moreover, the condensed polycyclic aromatic compound according to the present invention is preferably a compound represented by the following general formula (2).

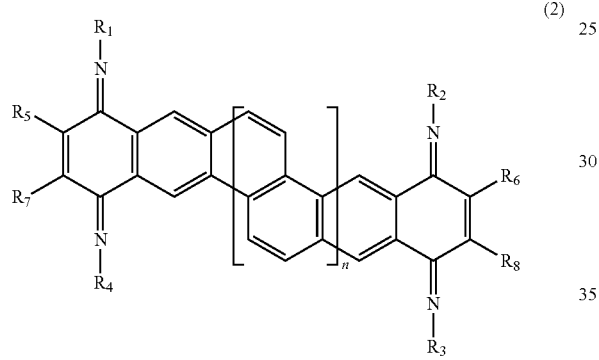

(2)

In general formula (2), $R_1$, $R_2$, $R_3$, $R_4$, $R_5$, $R_6$, $R_7$ and $R_8$ respectively and independently represent a hydrogen atom, substituted or unsubstituted aliphatic hydrocarbon group or substituted or unsubstituted aromatic hydrocarbon group, and n represents an integer of 1 to 10.

There are no particular limitations on $R_1$, $R_2$, $R_3$, $R_4$, $R_5$, $R_6$, $R_7$ and $R_8$ provided they are electron donating groups, and examples thereof respectively and independently include an alkyl group such as a methyl group, ethyl group, n-propyl group, isopropyl group, sec-butyl group, isobutyl group or tert-butyl group, a cycloalkyl group such as a cyclopentyl group or cyclohexyl group, an alkenyl group such as a vinyl group or allyl group, and an aryl group such as a phenyl group, tolyl group or naphthyl group.

There are no particular limitations on substituents of $R_1$, $R_2$, $R_3$, $R_4$, $R_5$, $R_6$, $R_7$ and $R_8$ when they are substituted with substituents, and examples thereof include aryl groups such as a phenyl group, tolyl group or naphthyl group, and alkoxy groups such as a methoxy group, ethoxy group, propoxy group, isopropoxy group, butoxy group, sec-butoxy group or tert-butoxy group.

$R_1$ to $R_4$ are more preferably aryl groups and even more preferably phenyl groups. $R_5$ to $R_8$ are more preferably alkyl groups and even more preferably methyl groups.

n is an integer of 1 to 10 that represents the degree of polymerization. n is preferably an integer of 5 or less.

Although the following indicates preferable examples of the condensed polycyclic aromatic compound according to the present invention, the condensed polycyclic aromatic compound according to the present invention is not limited thereto.

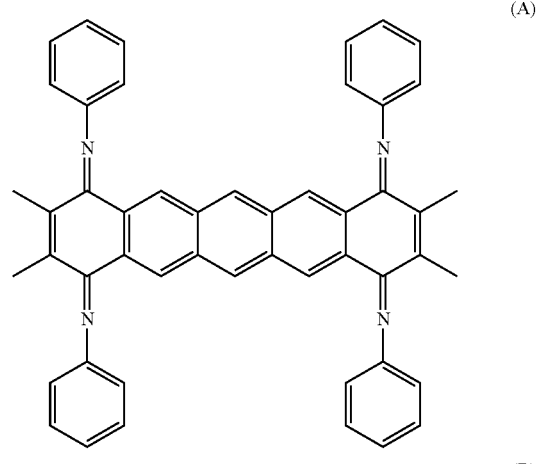

(A)

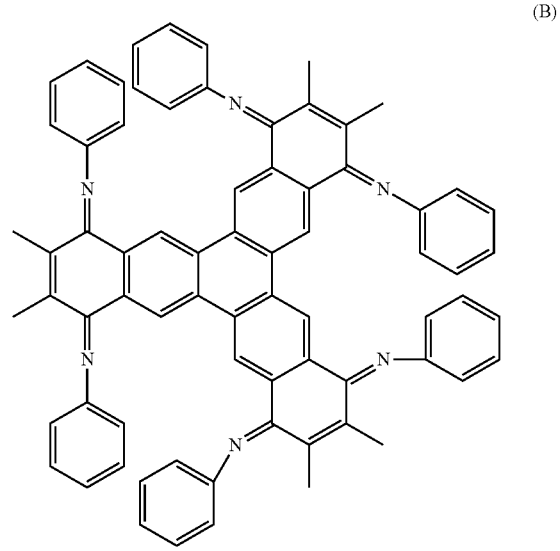

(B)

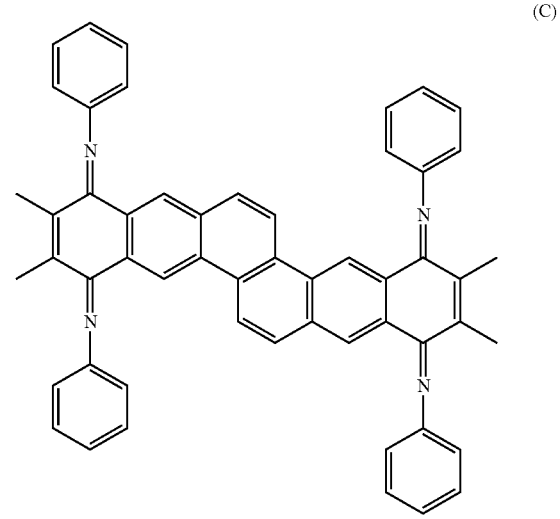

(C)

(D)

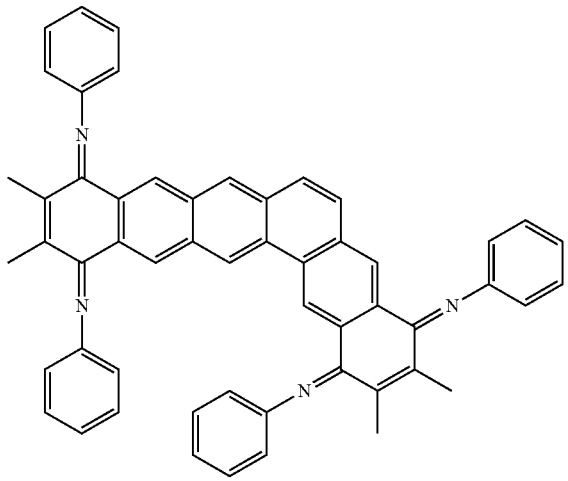

(E)

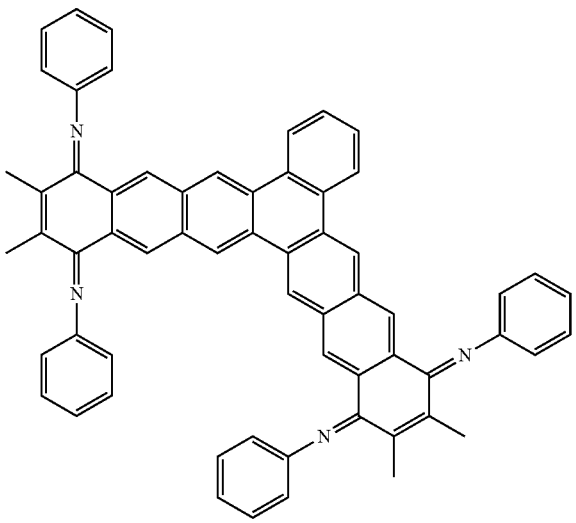

Next, the production process of the condensed polycyclic aromatic compound according to the present invention is described. The production process according to the present invention is characterized by reacting a compound having at least four oxo groups in a molecule thereof with an aniline-based compound in the presence of titanium tetrachloride and base. There are no particular limitations on the compound having at least four oxo groups in a molecule thereof used in the production process according to the present invention provided it has at least four oxo groups in a molecule thereof. Moreover, the aniline-based compound used in the production process according to the present invention may be a substituted aniline compound or an unsubstituted aniline compound. There are no particular limitations on the base provided it is a basic catalyst, and an example thereof is 1,4-diazabicyclo[2.2.2]octane (DABCO).

The production process of the condensed polycyclic aromatic compound according to the present invention is a production process of the condensed polycyclic aromatic compound of the present invention represented by general formula (1), and preferably consists of reacting a compound represented by the following general formula (3) with an aniline-based compound in the presence of titanium tetrachloride and base.

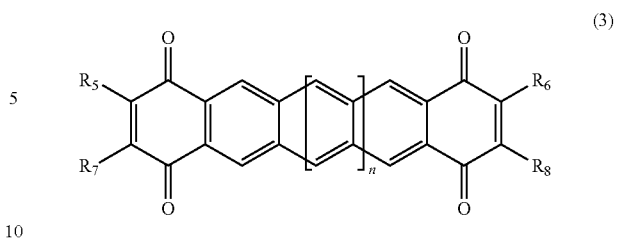

In general formula (3), $R_5$, $R_6$, $R_7$ and $R_8$ are the same as defined for $R_5$, $R_6$, $R_7$ and $R_8$ in general formula (1).

The production process of the condensed polycyclic aromatic compound according to the present invention is a production process of the condensed polycyclic aromatic compound of the present invention represented by general formula (2), and preferably consists of reacting a compound represented by the following general formula (4) with an aniline-based compound in the presence of titanium tetrachloride and base.

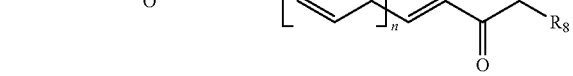

In general formula (4), $R_5$, $R_6$, $R_7$ and $R_8$ are the same as defined for $R_5$, $R_6$, $R_7$ and $R_8$ in general formula (2).

A compound having at least four oxo groups in a molecule thereof, a compound represented by general formula (3) and a compound represented by general formula (4) used in the production process according to the present invention can be synthesized by referring to the descriptions of non-patent documents consisting of JOC 1983, 48, 4358; JACS 1992, 114, 6330; J. Heterocyclic Chem., 2002, 39, 1093; and, JACS 1992, 114, 1388.

For example, in the case of 2,3,9,10-tetramethyl-1,4,8,11-pentacenetetrone, 1,4:5,8-diepoxy-1,4,5,8-tetrahydroanthracene can be synthesized from tetrabromobenzene and furan in accordance with the method described in a non-patent document (JOC 1983, 48, 4358), 1,4:8,11-dicarboxy-5,14:7,12-diepoxy-4a,5,7,7a,11a,12,14,14a-octahydro-1,2,3,4,8,9,10,11-octaphenylpentacene can be synthesized from 1,4:5,8-diepoxy-1,4,5,8-tetrahydroanthracene and 1,2,3,4-tetraphenylcyclopentadienone in accordance with the method described in a non-patent document (JACS 1992, 114, 6330), and 2,3,9,10-tetramethyl-1,4,8,11-pentacenetetrone can be synthesized from 1,4:8,11-dicarboxy-5,14:7,12-diepoxy-4a,5,7,7a,11a,12,14,14a-octahydro-1,2,3,4,8,9,10,11-octaphenylpentacene in accordance with the method described in a non-patent document (JACS 1992, 114, 1388).

(2) Positive Electrode Active Material for Lithium Ion Secondary Battery

The positive electrode active material for a lithium ion secondary battery according to the present invention is characterized by containing a condensed polycyclic aromatic compound having at least four imino groups in a molecule thereof, a condensed polycyclic aromatic compound represented by general formula (1), and a condensed polycyclic aromatic compound represented by general formula (2). A positive electrode active material for a lithium ion secondary battery refers to a material that is imparted directly to a positive electrode of a lithium ion secondary battery in an electrode reaction such as a charging reaction or discharging reaction of a lithium ion secondary battery.

(3) Positive Electrode for Lithium Ion Secondary Battery

The positive electrode for a lithium ion secondary battery according to the present invention is characterized by providing a condensed polycyclic aromatic compound having at least four imino groups in a molecule thereof, a condensed polycyclic aromatic compound represented by general formula (1), and a condensed polycyclic aromatic compound represented by general formula (2), or in other words, the positive electrode active material for a lithium ion secondary battery of the present invention, on at least the surface of a current collector.

A current collector refers to a chemically inert, highly conductive electron conductor for allowing current to continue to flow to an electrode during discharging or charging of a lithium ion secondary battery. The current collector is in the form of a foil or sheet and the like formed from the highly conductive electron conductor. Although there are no particular limitations on the form of the current collector provided it is compatible with the purpose of use, examples thereof include copper foil, aluminum foil and aluminum mesh.

An example of a method for providing the positive electrode active material on at least the surface of a current collector consists of coating the positive electrode active material onto the surface of the current collector. Coating refers to placing the positive electrode active material on the current collector. Although examples of coating methods include roll coating, dip coating, doctor blade coating, spray coating and curtain coating, there are no particular limitations thereon provided it is a coating method that is commonly used when fabricating electrodes for lithium ion secondary batteries.

The positive electrode for a lithium ion secondary battery according to the present invention may be provided with a conductive assistant on at least the surface of the current collector together with the positive electrode active material of the present invention. The conductive assistant is added to enhance electrical conductivity. Examples of conductive assistants include carbonaceous microparticles in the form of carbon black, graphite, acetylene black, Ketjen black or carbon fiber. These may be added alone or two or more types thereof may be added in combination. The amount added is preferably 10 parts by weight to 2000 parts by weight, more preferably 100 parts by weight to 1000 parts by weight, and even more preferably 200 parts by weight to 800 parts by weight per 100 parts by weight of the positive electrode active material of the present invention.

(4) Lithium Ion Secondary Battery

A lithium ion secondary battery according to the present invention is characterized by having at least a positive electrode, negative electrode and electrolyte as constituents thereof, wherein the positive electrode is the positive electrode of the present invention.

The negative electrode of the lithium ion secondary battery according to the present invention is preferably a lithium-based negative electrode. The lithium-based negative electrode can be composed with a lithium-based metal material in the manner of lithium metal or lithium alloy (such as Li—Al alloy), or a lithium-intercalated carbon material. A lithium-based metal material is preferably used in the form of a foil from the viewpoint of reducing the weight of the battery.

The electrolyte of the lithium ion secondary battery according to the present invention may be arranged between the positive electrode and the negative electrode, or may be arranged in the form of an electrolyte layer. The electrolyte is preferably composed of a polymer gel containing an electrolyte solution (polymer gel electrolyte). Examples of electrolytes contained in the polymer gel electrolyte include lithium salts such as $CF_3SO_3Li$, $C_4F_9SO_3Li$, $(CF_3SO_2)_2NLi$, $(CF_3SO_2)_3CLi$, $LiBF_4$, $LiPF_6$ and $LiClO_4$. The solvent used to dissolve the electrolyte is preferably a non-aqueous solvent. Examples of such non-aqueous solvents include linear carbonates, cyclic carbonates, cyclic esters, nitrile compounds, acid anhydrides, amide compounds, phosphate compounds and amine compounds. Specific examples of non-aqueous solvents include ethylene carbonate, propylene carbonate, diethyl carbonate, dimethoxyethane, γ-butyrolactone, N-methylpyrrolidinone, N,N'-dimethylacetoamide, mixtures of propylene carbonate and dimethoxyethane, mixtures of ethylene carbonate and diethyl carbonate, and mixtures of sulfolane and tetrahydrofuran.

Prepolymer TA210 (polyfunctional acrylate polymer having a polyoxyalkylene chain) polymerized with a photopolymerization initiator (such as Irgacure E184) is preferably used for the polymer gel, and copolymers of acrylonitrile and methyl acrylate or methacrylic acid are also used preferably. The polymer gel electrolyte can be obtained either by immersing a polymer in an electrolyte solution or polymerizing constituent units of a polymer (monomers/compounds) in the presence of an electrolyte solution. Moreover, the polyolefin-based gel described in Japanese Unexamined Patent Publication No. 2002-198095 is also used preferably. This gel is a non-crosslinked polymer grafted with a compound containing approximately 10% of an oligomer of polyethylene oxide such as polyethylene glycol in terms of the molar ratio of polyethylene. This polymer has completely different properties from non-grafted polyethylene in that it has the ability to retain an absorbed liquid as a result of gelling by absorbing a large amount of organic electrolyte solution. Thus, a gel electrolyte can be obtained by immersing the polymer in an electrolyte solution. In addition, a polymer gel electrolyte can be obtained that is integrated with a base material by applying to the base material a reaction mixture obtained by adding a crosslinking monomer to a solution in which the aforementioned non-crosslinked polymer has been dissolved in an electrolyte solution in an organic solvent, and providing reaction conditions that cause the crosslinking monomer to crosslink and polymerize.

The lithium ion secondary battery according to the present invention may also contain another constituent in the form of a separator. The separator can be used to prevent contact between the positive electrode and negative electrode of the lithium ion secondary battery, and may also contain electrolyte. Examples of separators include polypropylene porous film and non-woven fabric, and a polypropylene porous film is preferable.

The composed form (layered form) of the lithium ion secondary battery according to the present invention may be any arbitrary form. For example, a form may be employed in which the positive electrode of the present invention is impregnated with an electrolyte solution, a separator and glass filter are laminated onto the positive electrode, and the negative electrode is further laminated thereon, or a form may be employed in which a separator containing the positive electrode and electrolyte and a negative electrode are superimposed in that order.

The form of the lithium ion secondary battery according to the present invention may be a known form, an example of

13 which is a form in which an electrode laminate or wound body is sealed with a metal case, resin case or laminate film composed of a metal foil such as aluminum foil and a synthetic resin film. Moreover, examples of the external shape of the lithium ion secondary battery include, but are not limited to, a cylindrical shape, rectangular shape, coin shape or sheet.

EXAMPLES

The following indicates examples for providing a more detailed explanation of the present invention. Furthermore, the present invention is not limited to the following examples within a range that does deviate from the object and gist thereof.

Example 1-1

Synthesis Example 1

Synthesis of Condensed Polycyclic Aromatic Compound (5)>

Synthesis Example 1

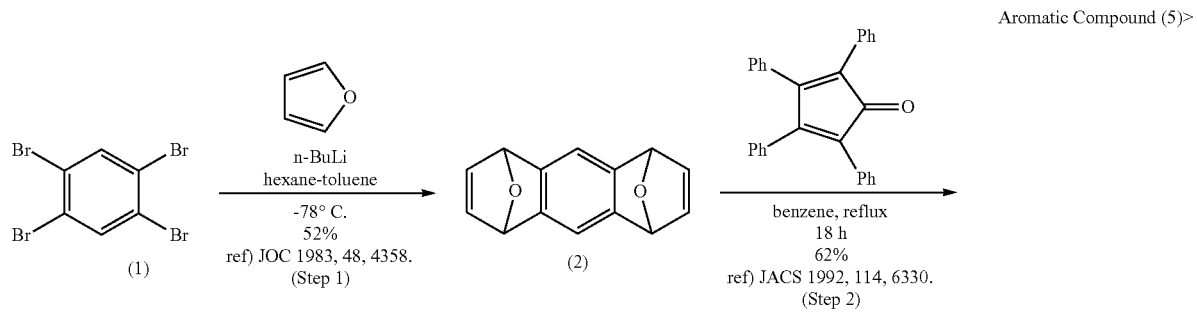

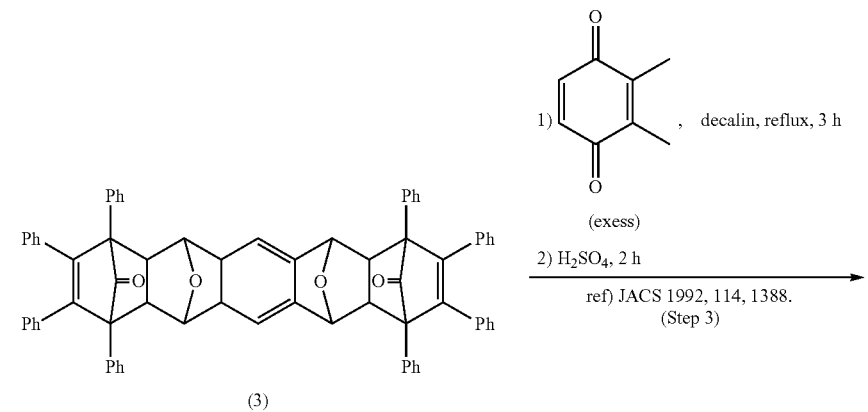

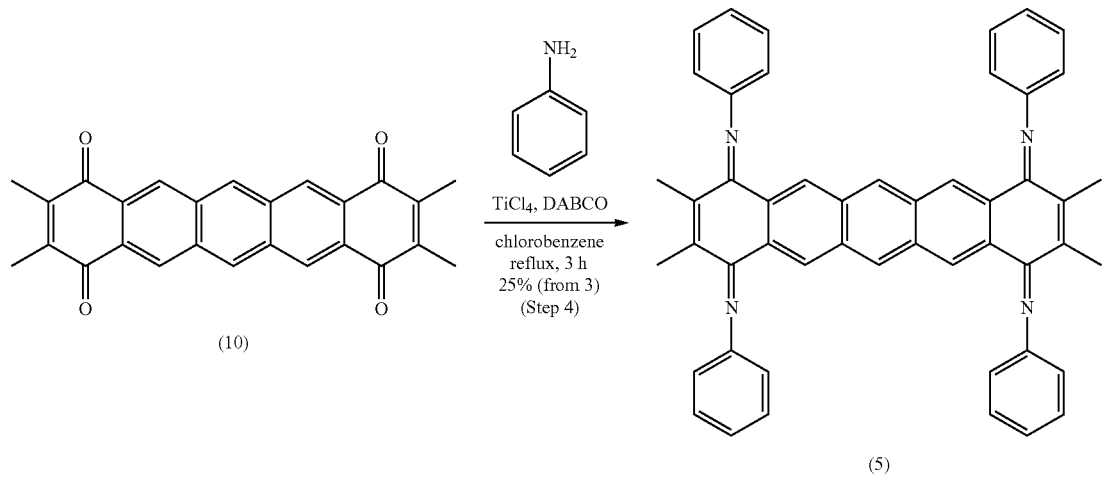

Condensed polycyclic aromatic compound (5) (N,N',N",N'"-tetramethyl-2,3,9,10-pentacenetetrone tetraimine) was synthesized from commercially available 1,2,4,5-tetrabromobenzene (1) according to a synthesis route composed of the four steps indicated below.

(Step 1) Synthesis of
1,4:5,8-diepoxy-1,4,5,8-tetrahydroanthracene (2)

1,4:5,8-diepoxy-1,4,5,8-tetrahydroanthracene (2) was synthesized from tetrabromobenzene (1) and furan in accordance with the method described in a non-patent document (JOC 1983, 48, 4358). Yield: 52%, spectral data: $^1$H-NMR (270 MHz, CDCl$_3$) δ 7.19 (s, 2H), 7.03 (s, 4H), 5.63 (s, 4H).

(Step 2) Synthesis of 1,4:8,11-dicarboxy-5,14:7,12-diepoxy-4a,5,7,7a,11a,12,14,14a-octahydro-1,2,3,4,8,9,10,11-octaphenylpentacene (3)

1,4:8,11-dicarboxy-5,14:7,12-diepoxy-4a,5,7,7a,11a,12,14,14a-octahydro-1,2,3,4,8,9,10,11-octaphenylpentacene (3) was synthesized from 1,4:5,8-diepoxy-1,4,5,8-tetrahydroanthracene (2) and 1,2,3,4-tetraphenylcyclopentadienone in accordance with the method described in a non-patent document (JACS 1992, 114, 6330). Yield: 62%, spectral data: $^1$H-NMR (270 MHz, CDCl$_3$) δ 7.58 (s, 2H), 7.46-7.30 (m, 20H), 7.01-6.88 (m, 20H), 5.84 (s, 4H), 3.07 (s, 4H).

(Step 3) Synthesis of
2,3,9,10-tetramethyl-1,4,8,11-pentacenetetrone (4)

Synthesis of 2,3-dimethyl-1,4-benzoquinone 2,3-dimethyl-1,4-benzoquinone was synthesized by oxidizing 2,3-dimethylhydroquinone in accordance with the method described in a non-patent document (J. Heterocyclic Chem. 2002, 39, 1093). Yield: 65%

Synthesis of
2,3,9,10-tetramethyl-1,4,8,11-pentacenetetrone (4)

2,3,9,10-tetramethyl-1,4,8,11-pentacenetetrone (4) was synthesized from 1,4:8,11-dicarboxy-5, 14:7,12-diepoxy-4a,5,7,7a,11a,12,14,14a-octahydro-1,2,3,4,8,9,10,11-octaphenylpentacene (3) in accordance with the method described in a non-patent document (JACS 1992, 114, 1388). The crude product thereof was used in the next step without additional purification. A mixture of 1,4:8,11-dicarboxy-5, 14:7,12-diepoxy-4a,5,7,7a,11a,12,14,14a-octahydro-1,2,3,4,8,9,10,11-octaphenylpentacene (3) (0.960 g, 0.98 mmol) and 2,3-dimethyl-1,4-benzoquinone (1.18 g, 8.67 mmol) dissolved in decalin (30 ml) was stirred for 3.5 hours at 200° C. After allowing the reaction mixture to cool to room temperature, the precipitate was collected by filtration, washed with hexane and CHCl$_3$, and dried in a vacuum. Concentrated H$_2$SO$_4$ (15 ml) was then added to the resulting gray solid. The reaction mixture was then stirred at room temperature. Two hours later, the reaction mixture was poured into ice water. The precipitate was collected by filtration and washed with H$_2$O and methanol to obtain a crude product (0.305 g). This crude product was used in the next step without additional purification.

(Step 4) Synthesis of N,N',N",N'"-tetraphenyl-2,3,9,10-tetramethyl-1,4,8,11-pentacenetetrone tetraimine (5)

A solution of TiCl$_4$ (0.25 ml, 2.3 mmol) dissolved in chlorobenzene (5 ml) was slowly added at 80° C. to a mixture of the crude pentacenetetrone (4) (0.126 g), aniline (0.100 g, 0.11 mmol) and 1,4-diazabicyclo[2.2.2]octane (DABCO) (1.3 g, 11.1 mmol) dissolved in chlorobenzene (25 ml). The reaction mixture was stirred for 3.5 hours at 130° C. The precipitate was then filtered with Celite and the resulting filtrate was concentrated. The residue was again dissolved in CHCl$_3$ and was re-precipitated in a large amount of acetonitrile. The product was purified by silica gel column chromatography (CHCl$_3$:hexane=3:1) to obtain N,N',N",N'"-tetraphenyl-2,3,9,10-tetramethyl-1,4,8,11-pentacenetetrone tetraimine (5) (0.0716 g, 0.103 mmol) at a yield of 25% with respect to 1,4:8,11-dicarboxy-5,14:7,12-diepoxy-4a,5,7,7a,11a,12,14,14a-octahydro-1,2,3,4,8,9,10,11-octaphenylpentacene (3).

Since the N,N',N",N'"-tetraphenyl-2,3,9,10-tetramethyl-1,4,8,11-pentacenetetrone tetraimine (5) is an E/Z isomer of imine bonding, it has the seven isomers indicated below. For this reason, the NMR spectrum of N,N',N",N'"-tetraphenyl-2,3,9,10-tetramethyl-1,4,8,11-pentacenetetrone tetraimine (5) demonstrated a plurality of peaks. Spectral data: $^1$H-NMR (500 MHz, CDCl$_3$) δ 8.90-8.80 (m, 26H), 2.38-1.48 (m, 12H); $^{13}$C-NMR (125 MHz, CDCl$_3$) δ 158.8, 151.6, 141.7, 130.4, 129.6, 129.1, 127.4, 125.0, 123.5, 120.0, 119.8, 15.8; IR (ATR, cm$^{-1}$) 2920, 2849, 1586, 1478, 1373, 1285, 1261, 1220, 1026, 922, 898, 835, 763, 693, 686, 663, 567, 505, 465, 429, 409, 402; elemental analysis: calculated values for C$_{50}$H$_{38}$N$_4$ (calcd): C, 86.42; H, 5.51, N, 8.06; measured values (found): C, 86.35; H, 5.53, N, 7.84; HRMS (ESI): calculated value for C$_{50}$H$_{39}$N$_4$ [M+H] (calcd): 695.3175, measured value (found): 695.3163.

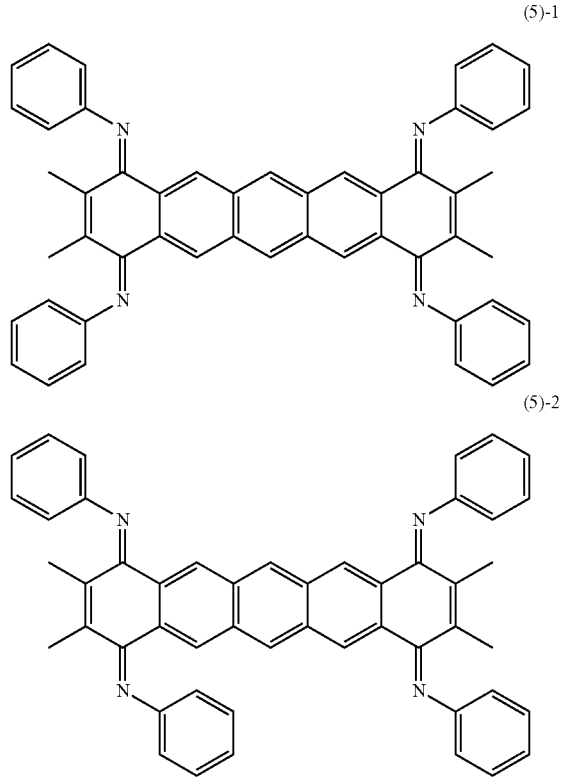

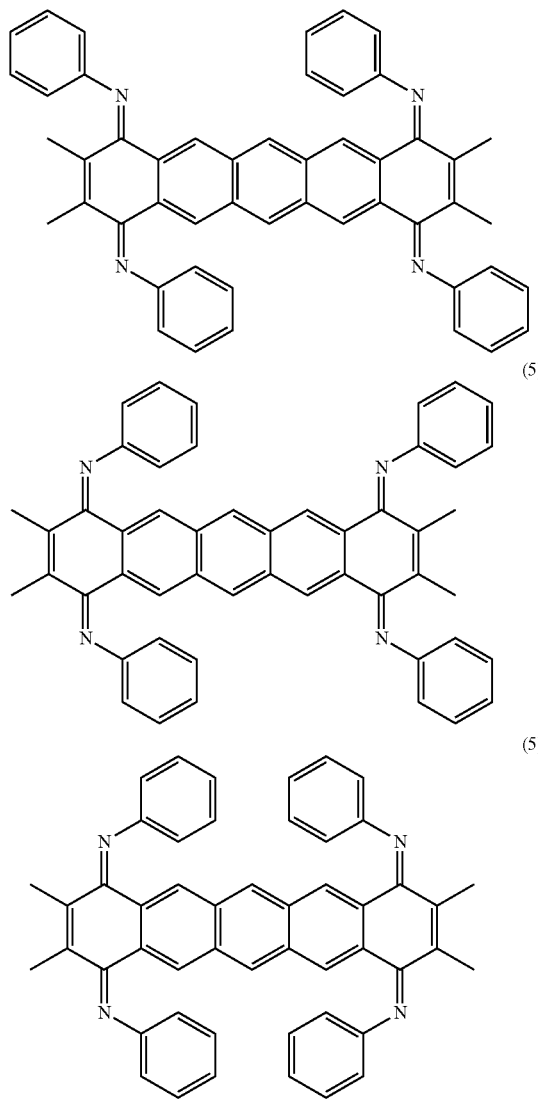
(5)-3
(5)-4
(5)-5
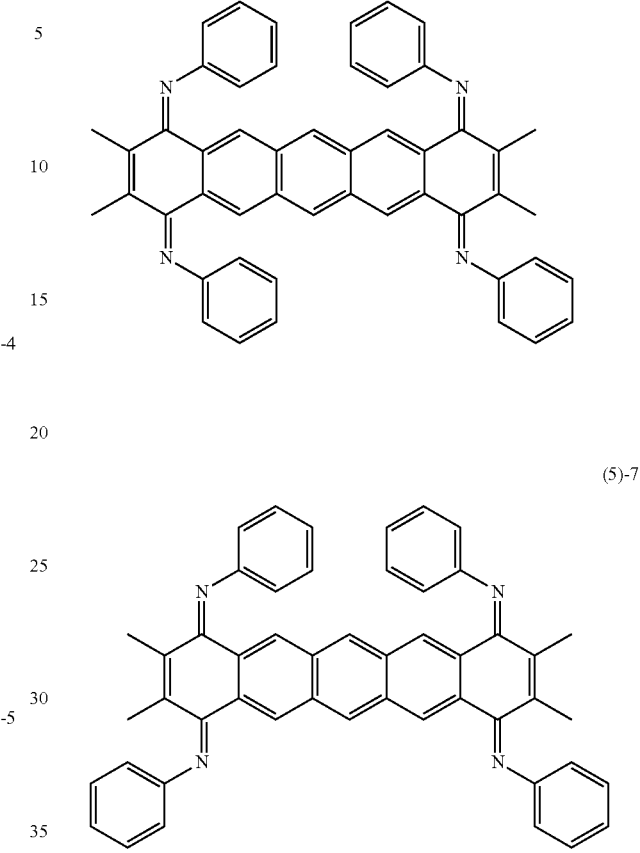
(5)-6
(5)-7
Example 1-2
Synthesis Example 2
Synthesis of Condensed Polycyclic
Aromatic Compound (11)>
Synthesis Example 2
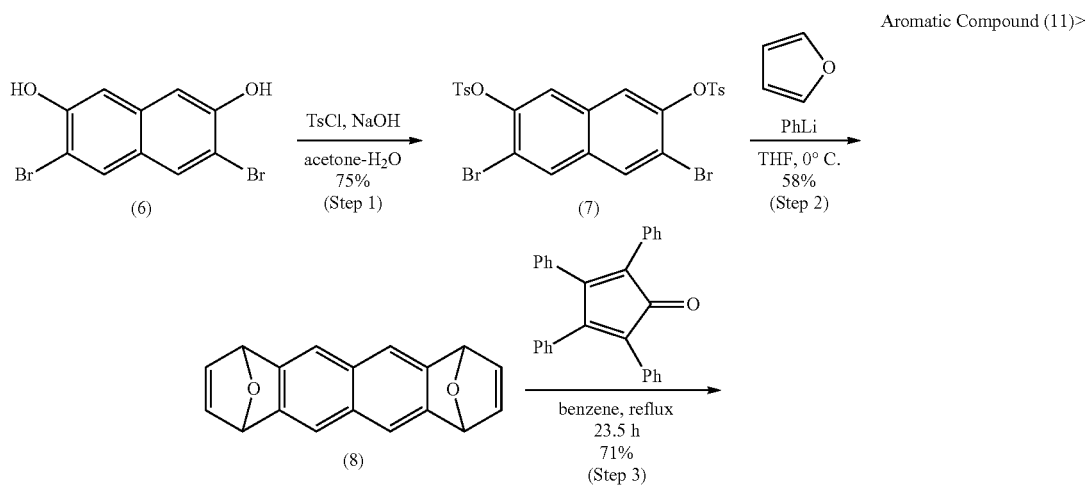

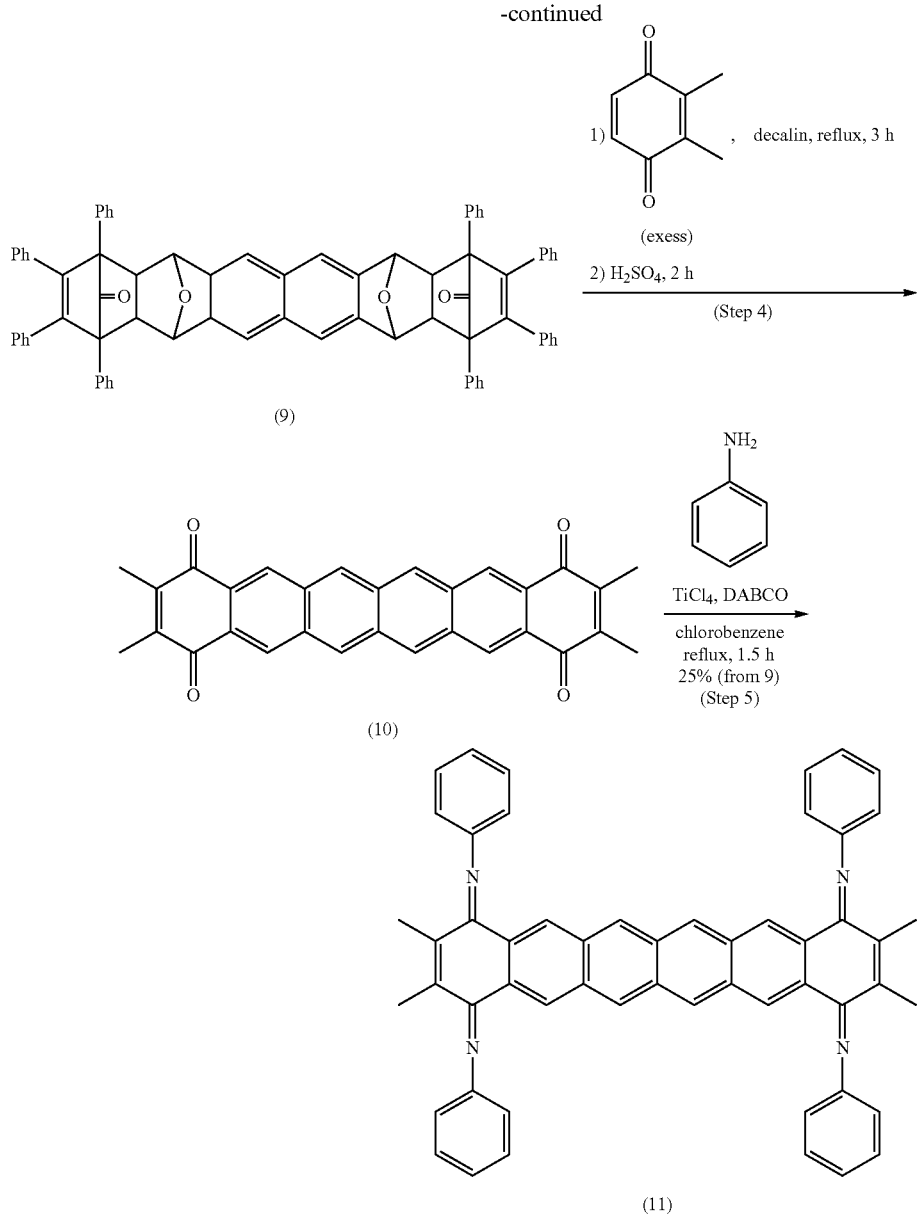

Condensed polycyclic aromatic compound (11) (N,N',N'',N'''-tetraphenyl-2,3,10,11-tetramethyl-1,4,9,12-hexacenetetrone tetraimine) was synthesized from commercially available 3,6-dibromo-2,7-dihydroxynaphthalene (6) according to a synthesis route composed of the four steps indicated below.

(Step 1) Synthesis of 3,6-dibromo-2,7-bis[(p-tolylsulfonyl)oxy]naphthalene (7)

3,6-dibromo-2,7-bis[(p-tolylsulfonyl)oxy]naphthalene (7) was synthesized by tosylating 3,6-dibromo-2,7-dihydroxynaphthalene (6) in accordance with the method described in a non-patent document (J. Org. Chem. 1985, 50, 2934). Yield: 75%, spectral data: $^1$H-NMR (270 MHz, CDCl$_3$) δ 7.19 (s, 2H), 7.82 (d, J=8.3 Hz, 4H), 7.74 (s, 2H), 7.35 (d, J=8.3 Hz, 4H), 2.48 (s, 6H).

(Step 2) Synthesis of 1,4:7,10-diepoxy-1,4,7,10-tetrahydrotetracene (8)

1,4:7,10-diepoxy-1,4,7,10-tetrahydrotetracene (8) was synthesized from 3,6-dibromo-2,7-bis[(tolylsulfonyl)oxo]naphthalene (7) and furan in accordance with the method described in a non-patent document (J. Org. Chem. 1985, 50, 2934). Yield: 58%

(Step 3) Synthesis of 1,4:9,12-dicarboxy-5,16:8,13-diepoxy-4a,5,8,8a,12a,13,16,16a-octahydro-1,2,3,4,9,10,11,12-octaphenylhexacene (9)

1,4:9,12-dicarboxy-5, 16:8,13-diepoxy-4a,5,8,8a,12a,13,16,16a-octahydro-1,2,3,4,9,10,11,12-octaphenylhexacene (9) was synthesized from 1,4:7,10-diepoxy-1,4,7,10-tetrahydrotetracene (8) and 1,2,3,4-tetraphenylcyclopentadienone in accordance with the method described in a non-patent document (JACS 1992, 114, 6330). A mixture of 1,4:7,10-diepoxy-1,4,7,10-tetrahydrotetracene (8) (0.2600 g, 1.0 mmol) and 1,2,3,4-tetraphenylcyclopentadienone (0.7961 g, 2.0 mmol) dissolved in benzene (20 ml) was stirred for 24 hours while refluxing. After adding methanol to the reaction mixture, the precipitate was collected by filtration, washed with methanol and dried in a vacuum to obtain a product in the form of 1,4:9,12-dicarboxy-5, 16:8,13-diepoxy-4a,5,8,8a,12a,13,16,16a-octahydro-1,2,3,4,9,10,11,12-octaphenylhexacene (9) (0.3926 g, 0.38 mmol) at a yield of 38%. The filtrate was then concentrated and the residue was purified by silica gel column chromatography ($CHCl_3$:hexane=3:1) to obtain 1,4:9,12-dicarboxy-5,16:8,13-4a,5,8,8a,12a,13,16,16a-octahydro-1,2,3,4,9,10,11,12-octaphenylhexacene (9) at a yield of 33%. The total yield of the product in the form of 1,4:9,12-dicarboxy-5,16:8,13-4a,5,8,8a,12a,13,16,16a-octahydro-1,2,3,4,9,10,11,12-octaphenylhexacene (9) was 71%. Spectral data: $^1$H-NMR (500 MHz, $CDCl_3$) δ 7.84 (s, 4H), 7.50-7.30 (m, 20H), 7.04-6.92 (m, 20H), 5.94 (s, 4H), 3.24 (s, 4H); $^{13}$C-NMR (125 MHz, $CDCl_3$) δ 196.7, 144.7, 138.7, 135.3, 132.6, 130.1, 129.8, 128.5, 127.7, 127.6, 127.0, 81.2, 64.6, 47.4; IR (ATR, $cm^{-1}$) 1771, 1497, 1444.71, 1026, 980, 900, 856, 841, 767, 746, 731, 696, 673, 660, 640, 572, 553, 507, 473, 460; elemental analysis: calculated values for $C_{76}H_{52}O_4$ (calcd): C, 88.69; H, 5.09; measured values (found): C, 88.12; H, 5.04.

(Step 4) Synthesis of
2,3,10,11-tetramethyl-1,4,9,12-hexacenetetrone (10)

2,3,10,11-tetramethyl-1,4,9,12-hexacenetetrone (10) was synthesized from 1,4:9,12-dicarboxy-5, 16:8,13-diepoxy-4a,5,8,8a,12a,13,16,16a-octahydro-1,2,3,4,9,10,11,12-octaphenylhexacene (9) using the same method as Scheme 1. The crude product was used in the next step without additional purification. A mixture of 1,4:9,12-dicarboxy-5,16:8,13-diepoxy-4a,5,8,8a,12a,13,16,16a-octahydro-1,2,3,4,9,10,11,12-octaphenylhexacene (9) (0.3080 g, 0.3 mmol) and 2,3-dimethyl-1,4-benzoquinone (0.3271 g, 2.4 mmol) dissolved in decalin (30 ml) was stirred for 3.5 hours at 200° C. After allowing the reaction mixture to cool to room temperature, the precipitate was collected by filtration, washed with hexane and $CHCl_3$, and dried in a vacuum. Concentrated $H_2SO_4$ (15 ml) was then added to the resulting gray solid. The reaction mixture was then stirred at room temperature. Two hours later, the reaction mixture was poured into ice water. The precipitate was then collected by filtration and washed with $H_2O$ and methanol to obtain a crude product (0.1206 g). This crude product was used in the next step without additional purification.

(Step 5) Synthesis of N,N',N'',N'''-tetraphenyl-2,3,10,11-tetramethyl-1,4,9,12-hexacenetetrone tetraimine (11)

A solution of $TiCl_4$ (0.15 ml, 1.4 mmol) dissolved in chlorobenzene (5 ml) was slowly added at 75° C. to a mixture of the crude hexacenetetrone (10) (0.118 g), aniline (0.15 ml, 1.6 mmol) and 1,4-diazabicyclo[2.2.2]octane (DABCO) (0.900 g, 8.0 mmol) dissolved in chlorobenzene (20 ml). The reaction mixture was then stirred for 1.5 hours at 125° C. This reaction mixture was then concentrated by passing through a silica gel column ($CHCl_3$). The residue was again dissolved in $CHCl_3$ and re-precipitated in a large amount of acetonitrile. The precipitate was then filtered with Celite, washed with acetonitrile and MeOH, and dried in a vacuum to obtain N,N',N'',N'''-tetraphenyl-2,3,10,11-tetramethyl-1,4,9,12-hexacenetetrone tetraimine (11) (0.0560 g, 0.075 mmol) at a yield of 25% with respect to 1,4:9,12-dicarboxy-5, 16:8,13-diepoxy-4a,5,8,8a,12a,13,16,16a-octahydro-1,2,3,4,9,10,11,12-octaphenylhexacene (9).

As a result of being an E/Z isomer of imine bonding in the same manner as N,N',N'',N'''-tetramethyl-2,3,9,10-tetramethyl-1,4,8,11-pentacenetetrone tetraimine (5), the N,N',N'',N'''-tetraphenyl-2,3,10,11-tetramethyl-1,4,9,12-hexacenetetrone tetraimine (11) has seven isomers. For this reason, the NMR spectrum of N,N',N'',N'''-tetraphenyl-2,3,10,11-tetramethyl-1,4,9,12-hexacenetetrone tetraimine (11) demonstrated a plurality of peaks. Spectral data: $^1$H-NMR (500 MHz, $CDCl_3$) δ 8.74-6.91 (m, 28H), 2.53-1.51 (m, 12H); $^{13}$C-NMR (125 MHz, $CDCl_3$) δ 159.6, 158.8, 158.6, 151.9, 151.3, 145.9, 141.7, 140.2, 135.7, 134.2, 132.5, 131.1, 130.7, 129.6, 129.3, 129.1, 128.9, 128.4, 126.5, 126.2, 125.2, 124.7, 124.6, 123.8, 123.4, 120.1, 119.6, 119.1, 18.2, 17.0, 15.9, 15.6; IR (ATR, $cm^{-1}$) 1585, 1496, 1480, 1446, 1424, 1375, 1298, 1259, 1225, 1169, 1070, 1026, 918, 895, 763, 749, 692, 502, 473, 458; elemental analysis: calculated values for $C_{54}H_{40}N_4 \cdot 3H_2O$ (calcd): C, 86.44; H, 5.45; N, 7.47; measured values (found): C, 86.44; H, 5.36; N, 7.28; HRMS (ESI): calculated value for $C_{54}H_{41}N_4$ [M+H] (calcd): 745.3331, measured value (found): 745.3348.

Example 1-3

Synthesis Example 3

Synthesis of Condensed Polycyclic Aromatic Compound (17)>

Synthesis Example 3

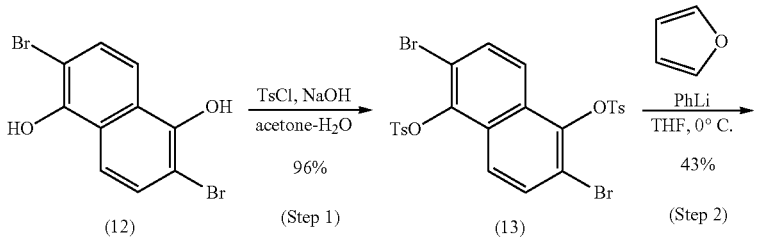

(12)  (Step 1)  (13)  (Step 2)

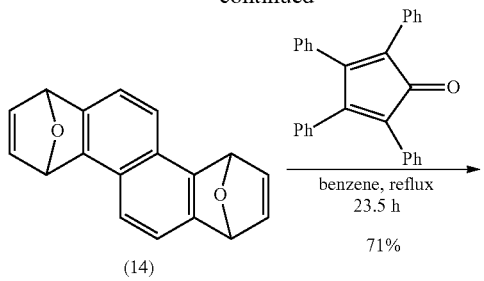

(Step 3)

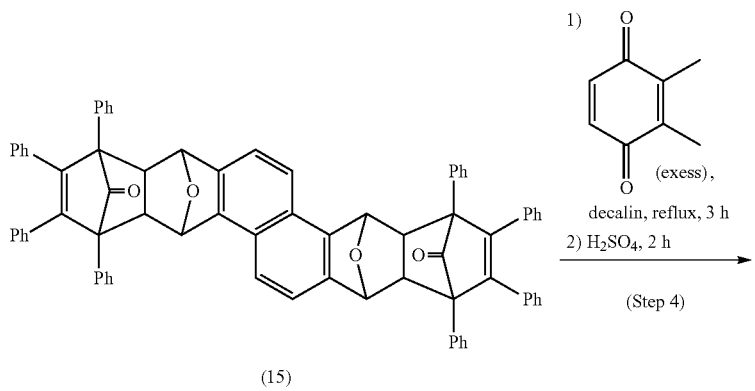

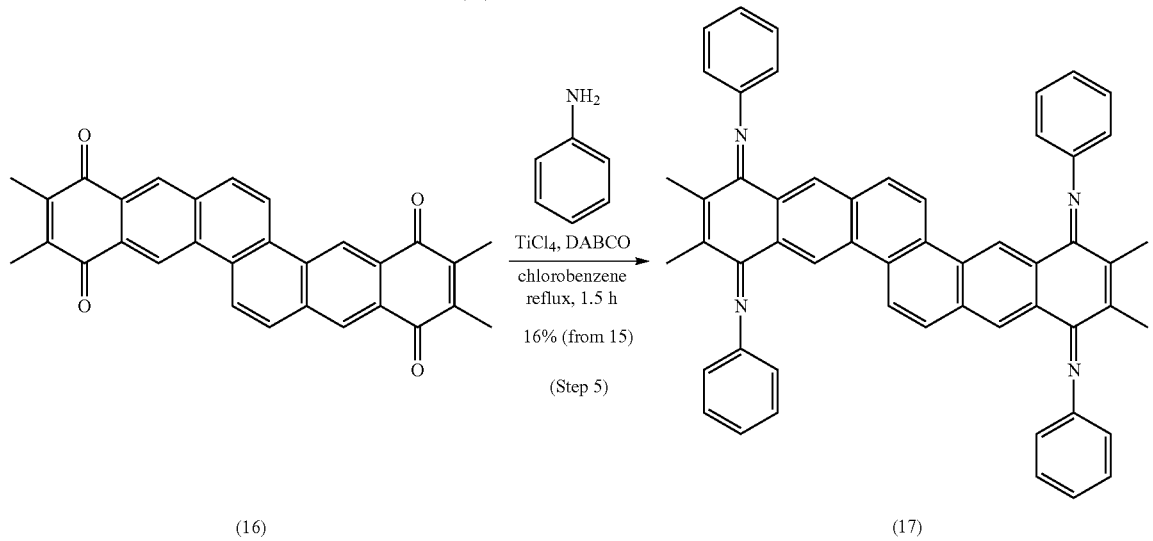

N,N',N'',N'''-tetraphenyl-2,3,10,11-tetramethyl-1,4,9,12-dibenzo[b,k]chrysenetetrone tetraimine (17) was synthesized from 2,6-dibromo-1,5-dihydroxynaphthalene (12) according to a synthesis route composed of the five steps indicated below.

(Step 1) Synthesis of 2,6-dibromo-1,5-bis[(p-tolylsulfonyl)oxo]naphthalene (13)

Synthesis of 2,6-dibromo-1,5-bis[(p-tolylsulfonyl)oxo] naphthalene (13) was synthesized by tosylating 2,6-dibromo-1,5-dihydronaphthalene (12) in accordance with the method described in a non-patent document (J. Org. Chem. 1983, 48, 1682). Yield: 96%

(Step 2) Synthesis of 1,4:7,10-diepoxy-1,4,7,10-tetrahydrochrysene (14)

1,4:7,10-diepoxy-1,4,7,10-tetrahydrochrysene (14) was synthesized from 2,6-dibromo-1,5-bis[(p-tolylsulfonyl)oxo] naphthalene (13) and furan in accordance with the method described in a non-patent document (J. Org. Chem. 1982, 48, 1683). Yield: 43%

(Step 3) Synthesis of 1,4:9,12-dicarboxy-5, 16:8,13-diepoxy-4a,5,8,8a,12a,13,16,16a-octahydro-1,2,3,4,9,10,11,12-octaphenyldibenzo[b,k]chrysene (15)

1,4:9,12-dicarboxy-5, 16:8,13-diepoxy-4a,5,8,8a,12a,13, 16,16a-octahydro-1,2,3,4,9,10,11,12-octaphenyldibenzo[b, k]chrysene (15) was synthesized from 1,4:7,10-diepoxy-1,4, 7,10-tetrahydrochrysene (14) and 1,2,3,4-tetraphenylcyclopentadienone in accordance with the method described in a non-patent document (JACS 1992, 114, 6330). A mixture of 1,4:7,10-diepoxy-1,4,7,10-tetrahydrochrysene (14) (0.6336 g, 2.4 mmol) and 1,2,3,4-tetraphenylcyclopentadienone (1.872 g, 4.9 mmol) dissolved in benzene (45 ml) was stirred for 28 hours while refluxing. After adding methanol, the precipitate was collected by filtration, washed with methanol and dried in a vacuum to obtain a product in the form of 1,4:9,12-dicarboxy-5, 16:8,13-diepoxy-4a,5,8,8a,12a,13,16, 16a-octahydro-1,2,3,4,9,10,11,12-octaphenyldibenzo[b,k] chrysene (15) (1.7882 g, 1.7 mmol) at a yield of 71%. Spectral data: $^1$H-NMR (500 MHz, CDCl$_3$) δ 8.02 (s, 1H), 8.01 (s, 1H), 7.84 (s, 1H), 7.82 (s, 1H), 7.54-7.28 (m, 20H), 7.04-6.93 (m, 20H), 6.33 (s, 2H), 6.03 (s, 2H), 3.10 (m, 4H); $^{13}$C-NMR (125 MHz, CDCl$_3$) δ 196.5, 144.9, 144.5, 138.8, 138.6, 135.5, 135.3, 130.1, 130.0, 129.7, 129.6, 128.5, 128.4, 127.7, 127.6, 127.5, 125.7, 123.5, 119.2, 82.1, 80.3, 64.6, 64.5, 45.6, 46.1; IR (ATR, cm$^{-1}$) 1773, 1497, 1444, 1029, 981, 926, 879, 842, 816, 774, 755, 731, 694, 680, 644, 572, 558, 530, 513, 494; elemental analysis: calculated values for C$_{78}$H$_{52}$O$_4$ (calcd): C, 88.69, H, 5.09; measured values (found): C, 88.60; H, 5.10.

(Step 4) Synthesis of 2,3,10,11-tetramethyl-1,4,9,12-dibenzo[b,k]chrysenetetrone (16)

2,3,10,11-tetramethyl-1,4,9,12-dibenzo[b,k]chrysenetetrone (16) was synthesized from 1,4:9,12-dicarboxy-5, 16:8,13-diepoxy-4a,5,8,8a,12a,13,16,16a-octahydro-1,2,3, 4,9,10,11,12-octaphenyldibenzo[b,k]chrysene (15) using the same method as Scheme 1. The crude product was used in the next step without additional purification. A mixture of 1,4:9, 12-dicarboxy-5, 16:8,13-diepoxy-4a,5,8,8a,12a,13,16,16a-octahydro-1,2,3,4,9,10,11,12-octaphenyldibenzo[b,k]chrysene (15) (0.750 g, 0.73 mmol) and 2,3-dimethyl-1,4-benzoquinone (0.800 g, 5.8 mmol) dissolved in decalin (17 ml) was stirred for 3 hours while refluxing. After allowing the reaction mixture to cool to room temperature, the precipitate was collected by filtration, washed with hexane and CHCl$_3$ and dried in a vacuum. Concentrated H$_2$SO$_4$ (5 ml) was then added to the resulting gray solid. The reaction mixture was then stirred at room temperature. One hour later, the reaction mixture was poured into ice water. The precipitate was collected by filtration and washed with H$_2$O and methanol to obtain a crude product (0.391 g). This crude product was used in the next step without additional purification.

(Step 5) Synthesis of N,N',N'',N'''-tetraphenyl-2,3,10, 11-tetramethyl-1,4,9,12-dibenzo[b,k]chrysenetetrone tetraimine (17)

A solution of TiCl$_4$ (0.4 ml, 3.65 mmol) dissolved in chlorobenzene (10 ml) was slowly added at 70° C. to a mixture of the crude dibenzo[b,k]chrysenetetrone (16) (0.391 g), aniline (0.5 ml, 4.56 mmol) and 1,4-diazabicyclo[2.2.2]octane (DABCO) (3.000 g, 26.75 mmol) dissolved in chlorobenzene (60 ml). The reaction mixture was then stirred for 2.5 hours at 125° C. The reaction mixture was then concentrated by passing through Celite and a silica gel column. The residue was then purified by flash silica gel column chromatography (CHCl$_3$) to obtain N,N',N'',N'''-tetraphenyl-2,3,10,11-tetramethyl-1,4,9,12-dibenzo[b,k]chrysenetetrone tetraimine (17) (0.0869 g, 0.012 mmol) at a yield of 16% with respect to 1,4:9,12-dicarboxy-5, 16:8,13-diepoxy-4a,5,8,8a,12a,13,16, 16a-octahydro-1,2,3,4,9,10,11,12-octaphenyldibenzo[b,k]chrysene (15).

As a result of being an E/Z isomer of imine bonding in the same manner as N,N',N'',N'''-tetramethyl-2,3,9,10-tetramethyl-1,4,8,11-pentacenetetrone tetraimine (5), N,N',N'',N'''-tetraphenyl-2,3,10,11-tetramethyl-1,4,9,12-dibenzo[b,k] chrysenetetrone tetraimine (17) has seven isomers. For this reason, the NMR spectrum of N,N',N'',N'''-tetraphenyl-2,3, 10,11-tetramethyl-1,4,9,12-dibenzo[b,k]chrysenetetrone tetraimine (17) demonstrated a plurality of peaks. Spectral data: $^1$H-NMR (500 MHz, CDCl$_3$) δ 9.54-6.90 (m, 28H), 2.43-1.52 (m, 12H); $^{13}$C-NMR (125 MHz, CDCl$_3$) δ 158.6, 158.2, 152.3, 151.8, 141.3, 141.1, 130.7, 129.8, 129.6, 129.1, 128.2, 127.9, 127.7, 125.4, 123.6, 123.5, 122.5, 120.2, 119.7, 119.4, 118.8, 15.7; IR (ATR, cm$^{-1}$) 1619, 1589, 1480, 1448, 1373, 1296, 1273, 1221, 1071, 1031, 908, 896, 875, 815, 766, 730, 717, 694, 560, 506; elemental analysis: calculated values for C$_{54}$H$_{40}$N$_4$ (calcd): C, 87.07; H, 5.41, N, 7.52; measured values (found): C, 86.73; H, 5.39, N, 7.23; HRMS (ESI): calculated value for C$_{54}$H$_{41}$N$_4$ [M+H] (calcd): 745.3331, measured value (found): 745.3361.

Example 2

Electrochemical Reduction Reaction of Condensed Polycyclic Aromatic Compound (5): Elongation of Condensed Ring (Acene) Backbone The condensed polycyclic aromatic compound (5) (1.40 mg) was dissolved in an acetonitrile solution containing 0.5 M (mol/l) trifluoroacetic acid (Kanto Chemical) and 0.2 M (mol/l) TBABF4 (tetrabutylammonium tetrafluoroborate, Fluka) and brought to a volume of 10 ml. A platinum mesh electrode was used for the working electrode, an Ag/Ag$^+$ electrode was used for the reference electrode, a platinum coil was used for the counter electrode, and the condensed polyacrylic aromatic compound (5) was electrochemically reduced by applying an electric potential of −0.1 V (versus Ag/Ag$^+$) with a potentiostat. As a result, the reduced form of the condensed polycyclic aromatic compound (5) in the form of condensed polycyclic aromatic compound (5Red) was formed in the system according to the reaction indicated below. The formation process was confirmed with a spectrophotometer (Shimadzu). The visible-ultraviolet spectra are shown in FIG. 1. As is clear from FIG. 1, the characteristic benzene spectrum of the condensed polycyclic aromatic compound (5) was generated, thereby confirming the formation of the condensed polycyclic aromatic compound (5). The results of the electrochemical reduction reaction of the condensed polycyclic aromatic compound (5) to the condensed polycyclic aromatic compound (5Red) are shown below.

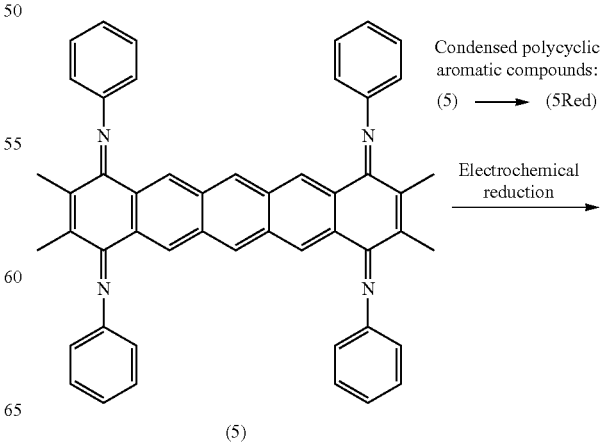

(5)

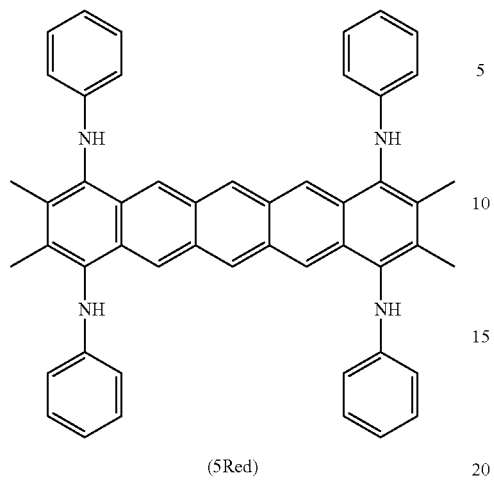

(5Red)

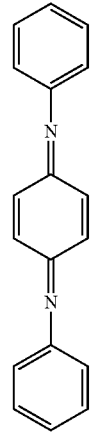

a

Example 3

Evaluation of Multi-Electron Transfer

Condensed polycyclic aromatic compound (5) (1.39 mg), condensed polycyclic aromatic compound (11) (1.49 mg) and condensed polycyclic aromatic compound (17) (1.49 mg) were respectively dissolved in an acetonitrile solution containing 1 M (mol/l) trifluoroacetic acid (Kanto Chemical) and 0.2 M (mol/l) TBABF4 (tetrabutylammonium tetrafluoroborate, Fluka) to prepare a 0.2 mM solutions (10 ml) of the three condensed polycyclic aromatic compounds. Each of the solutions was subjected to cyclic voltammetry using an electrochemical measurement device (BAS) under conditions of a sweep rate of 0.1 V/s, use of glassy carbon for the working electrode, use of a platinum electrode for the counter electrode, use of a Pt coil for the auxiliary electrode, and use of an Ag/Ag$^+$ electrode for the reference electrode. Electric potential was corrected by ferrocene/ferrocenium oxidation-reduction.

Comparative Example 1

A 0.2 mM solution (25 ml) of the following compound a was prepared using the exact same method as Example 3 with the exception of using compound a (1.29 mg) instead of condensed polycyclic aromatic compound (5), condensed polycyclic aromatic compound (11) and condensed polycyclic aromatic compound (17), followed by subjecting the solution to cyclic voltammetry under the exact same conditions as Example 3. Compound a was synthesized with reference to a non-patent document (C. C. Han, R. Balakumar, D. Thirumalai and M. T. Chung, Org. Biomol. Chem. 2006, 4, 3511-3516) (yield: 67%).

<Results of Evaluating Multi-Electron Transfer>

Figure 2:
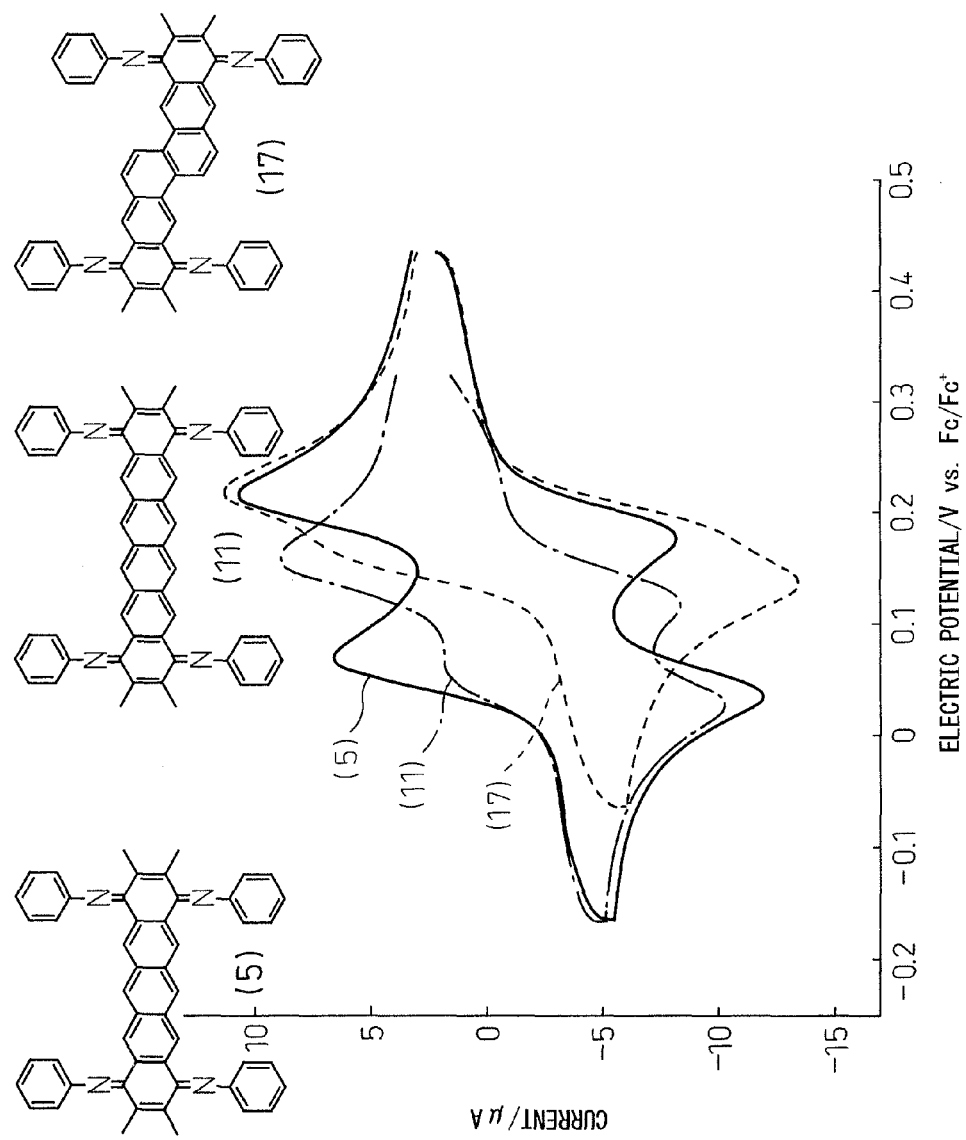

FIG. 2-1 shows the results of cyclic voltammetry for condensed polycyclic aromatic compound (5) and compound a. Compound a demonstrated two-step peaks respectively indicating the transfer of one electron. Condensed polycyclic aromatic compound (5) demonstrated two-step peaks. Since each of these peak current values ($I_{pa}$ and $I_{pc}$) was roughly twice the peak current values of compound a, each one-step peak was determined to correspond to a two-electron reaction. In addition, the potential difference of each peak was 40 mV on the high potential side and 34 mV on the low potential side. Each of these peaks was determined to indicate one-step, two-electron transfer. Condensed polycyclic aromatic compound (5) was confirmed to allow the transfer of four electrons with a single molecule. FIG. 2-2 shows the results of cyclic voltammetry for condensed polycyclic aromatic compounds (5), (11) and (17). As is clear from FIG. 2-2, the condensed polycyclic aromatic compounds (II) and (17) were determined to contain two cycles of one-step, two-electron transfer processes similar to that of condensed polycyclic aromatic compound (5) within the extremely narrow range of 0.2 volts (V), and the condensed polycyclic aromatic compounds (II) and (17) were also confirmed to allow the transfer of four electrons with a single molecule.

Example 4

Example 4-1

Fabrication of Electrode for Positive Electrode of Lithium Ion Secondary Battery The condensed polycyclic aromatic compound (5) (2 mg) synthesized in the manner previously described, Ketjen black (Ketjen Black International, 4 mg) and electrically conductive binder (TAB-2, Housen, 4 mg) were mixed and formed into a sheet followed by pressing onto the surface of a current collector in the form of aluminum mesh (14φ, Nilaco). This was then vacuum-dried for 6 hours at 120° C. to fabricate an electrode provided with the condensed polycyclic aromatic compound (5).

<Fabrication of Coin-Shaped Lithium Ion Secondary Battery>

The aforementioned electrode was used as the positive electrode of a coin-shaped lithium ion secondary battery, and the positive electrode was impregnated with an electrolyte solution (Kishida Chemical) in the form of mixed solution of ethylene carbonate (EC) and diethylcarbonate (DEC) (EC: DEC=1:1 (volume ratio)) containing 1 M (mol/l) LiPF$_6$ (lithium hexafluorophosphate) salt electrolyte. A separator (Celgard) composed of a propylene porous film and a glass filter (Advantech) were laminated onto the positive electrode, followed by further laminating a negative electrode in the form of lithium foil (Honjo Metal) thereon. Subsequently, a coin-shaped aluminum case was superimposed in a state of having an insulating packing arranged around the periphery thereof, and pressure was applied with a clamp to fabricate a sealed, coin-shaped lithium ion secondary battery using the condensed polycyclic aromatic compound (5) for the positive electrode active material and using lithium metal for the negative electrode active material.

Example 4-2

Fabrication of Electrode for Positive Electrode of Lithium Ion Secondary Battery An electrode provided with the condensed polycyclic aromatic compound (11) was fabricated using the same method as Example 4-1 with the exception of using the condensed polycyclic aromatic compound (11) instead of the condensed polycyclic aromatic compound (5).

<Fabrication of Coin-Shaped Lithium Ion Secondary Battery>

A sealed, coin-shaped lithium ion secondary battery was fabricated according to the same method as Example 4-1 using the aforementioned electrode for the positive electrode of the coin-shaped battery, the condensed polycyclic aromatic compound (11) for the positive electrode active material, and lithium metal for the negative electrode active material.

Example 4-3

Fabrication of Electrode for Positive Electrode of Lithium Ion Secondary Battery An electrode provided with the condensed polycyclic aromatic compound (17) was fabricated using the same method as Example 4-1 with the exception of using the condensed polycyclic aromatic compound (17) instead of the condensed polycyclic aromatic compound (5).

<Fabrication of Coin-Shaped Lithium Ion Secondary Battery>

A sealed, coin-shaped lithium ion secondary battery was fabricated according to the same method as Example 4-1 using the aforementioned electrode for the positive electrode of the coin-shaped battery, the condensed polycyclic aromatic compound (17) for the positive electrode active material, and lithium metal for the negative electrode active material.

Comparative Example 2

Fabrication of Electrode for Positive Electrode of Lithium Ion Secondary Battery An electrode provided with the following compound b was fabricated using the exact same method as Example 4-1 with the exception of using the compound b having two imine bonds in a molecule thereof instead of the condensed polycyclic aromatic compound (5). Compound b was synthesized with reference to a non-patent document (H. K. Hall, Jr., A. B. Padias, P. A. Williams, J. M. Gosau, H. W. Boone, D. K. Park, Macromolecules 1995, 28, 1-8) (yield: 61%).

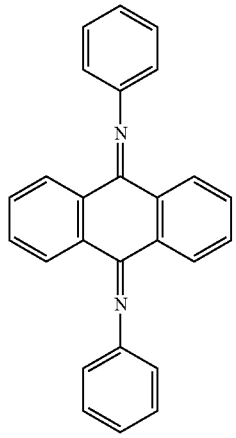

<Fabrication of Coin-Shaped Lithium Ion Secondary Battery>

A sealed, coin-shaped lithium ion secondary battery was fabricated according to the exact same method as Example 4-1 using the aforementioned electrode for the positive electrode of the coin-shaped battery, compound b for the positive electrode active material, and lithium metal for the negative electrode active material.

<Charge-Discharge Tests Using Coin-Shaped Lithium Ion Secondary Batteries Fabricated in Examples 4-1 to 4-3 and Comparative Example 2>

Charge-discharge tests were carried out according to the method described below using the coin-shaped lithium ion secondary batteries fabricated in Examples 4-1 to 4-3 and Comparative Example 2.

The coin-shaped lithium ion secondary batteries fabricated in Examples 4-1 to 4-3 and Comparative Example 2 were discharged to 2 volts (V) at a constant current of 0.05 milliamperes (mA) at a temperature of 25° C., and after pausing for 5 minutes, the batteries were charged to 4 volts (V) at a constant current of 0.05 milliamperes (mA). Charge-discharge tests were carried out for 100 cycles of the aforementioned discharging and charging.

<Results of Charge-Discharge Tests Using Coin-Shaped Lithium Ion Secondary Batteries Fabricated in Examples 4-1 to 4-3 and Comparative Example 2>

Figure 3:
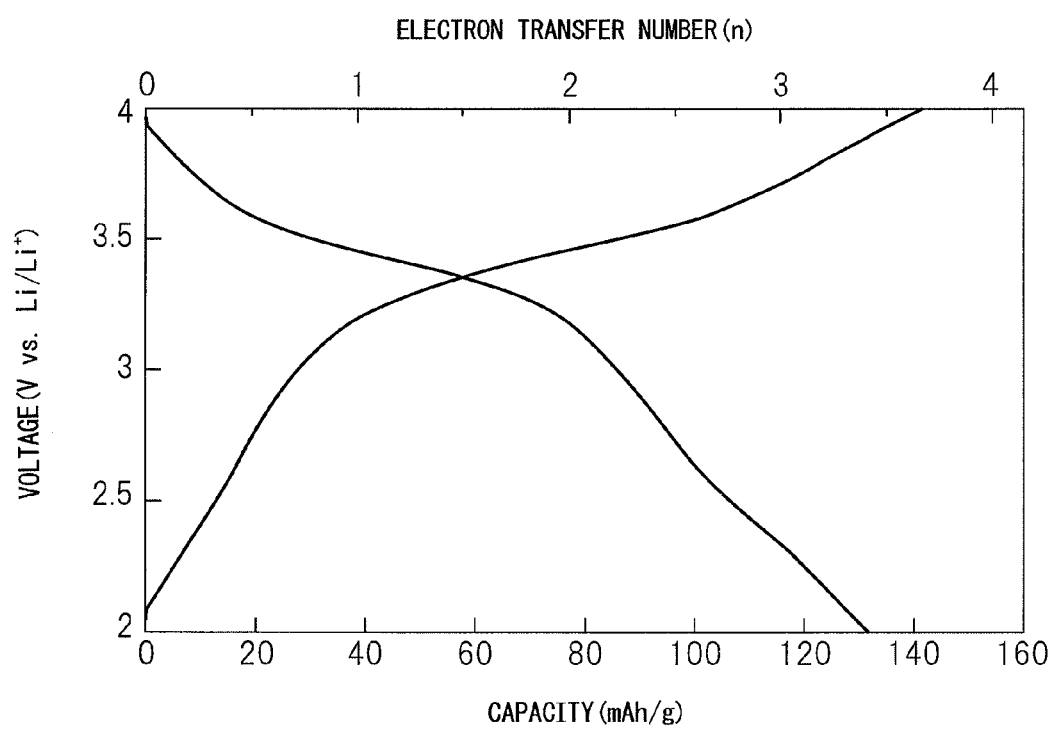
FIG. 3 is a graph showing charge-discharge curves for the 10th cycle of a coin-shaped lithium ion secondary battery fabricated in Example 4-1.
Figure 4:
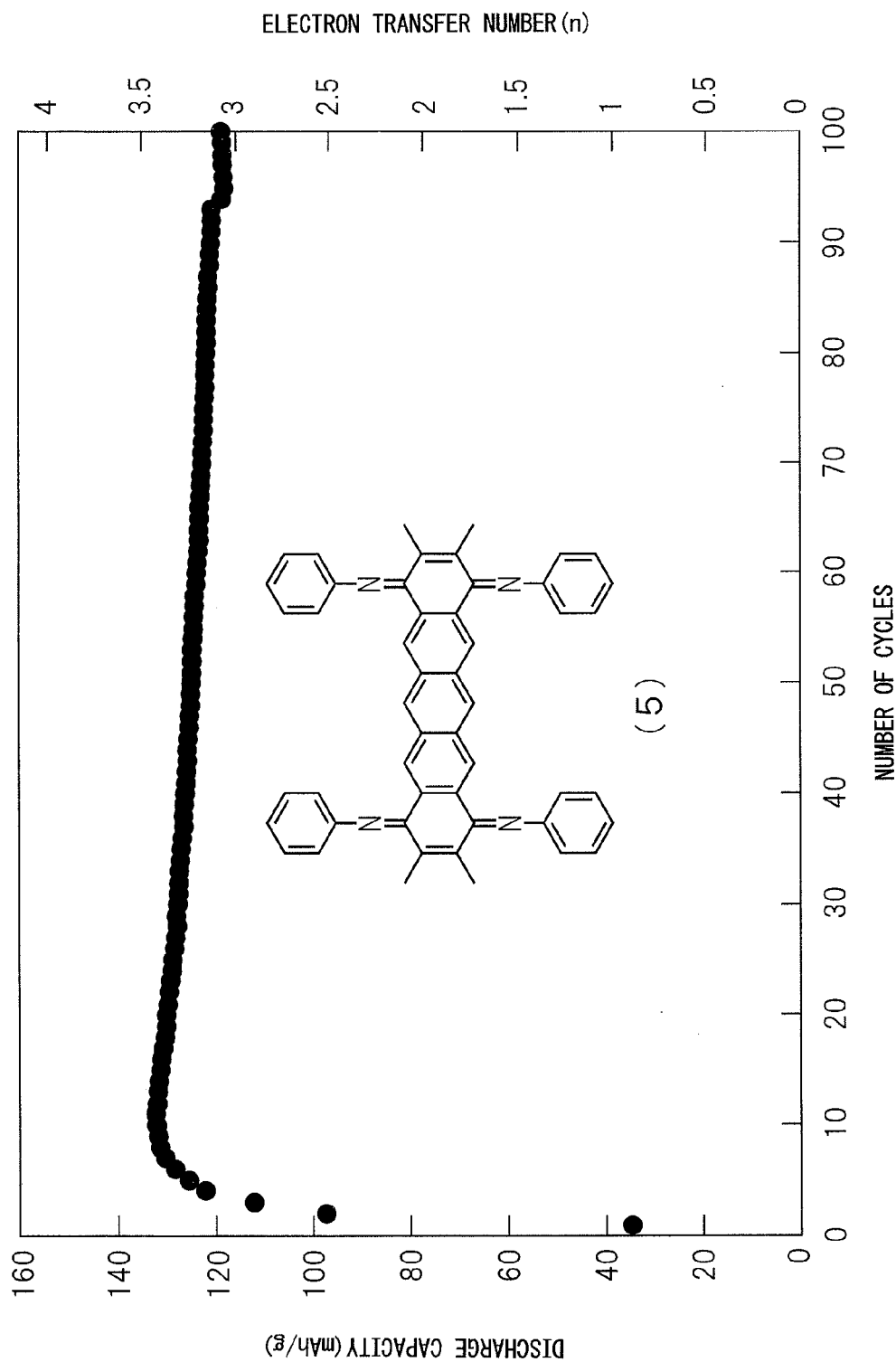
FIG. 4 is a graph showing discharge capacity through 100 cycles of a coin-shaped lithium ion secondary battery fabricated in Example 4-1.
Figure 5:
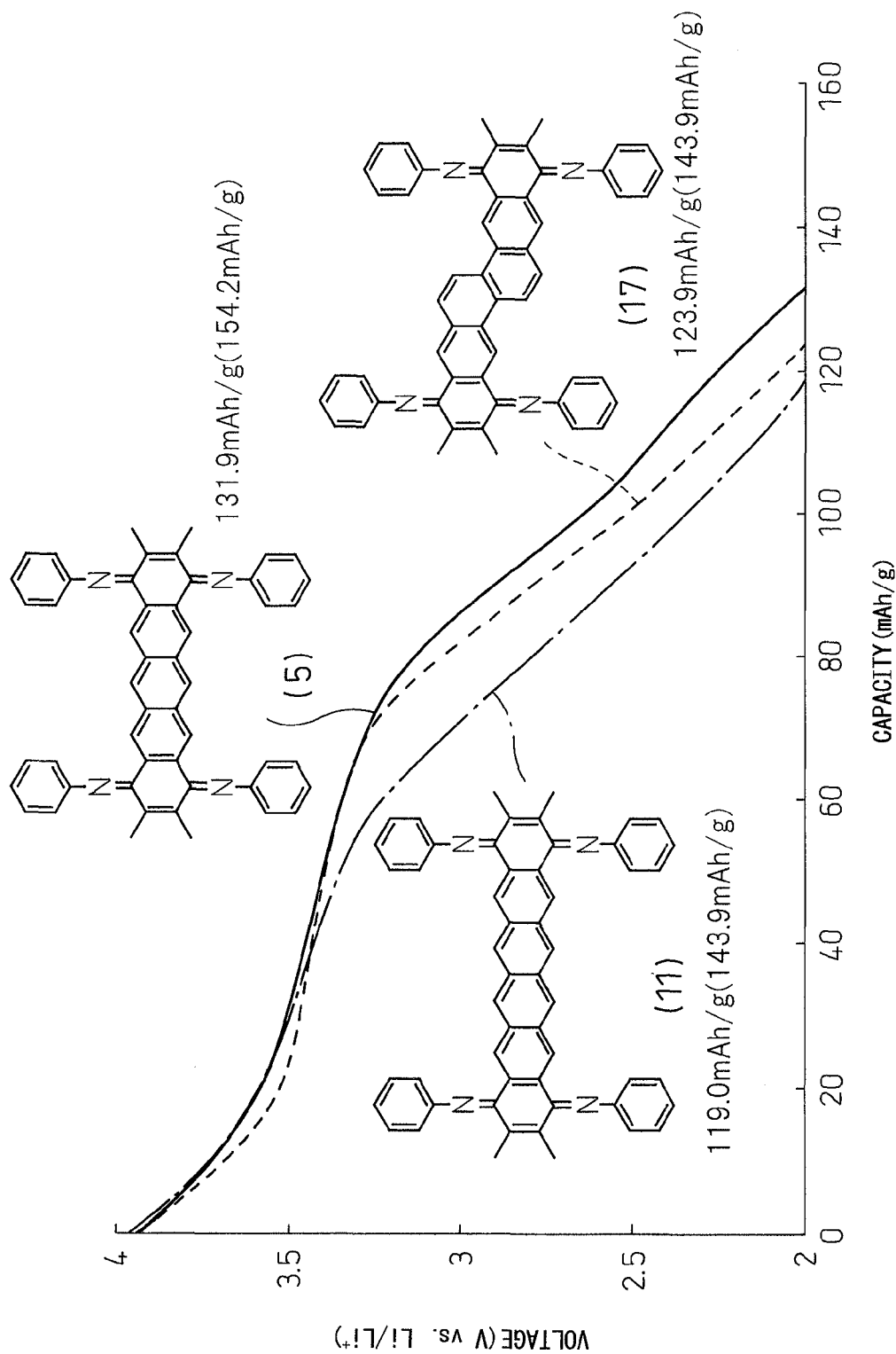
FIG. 5 is a graph showing discharge curves for the 10th cycle of coin-shaped lithium ion secondary batteries fabricated in Examples 4-1, 4-2 and 4-3.
Figure 6:
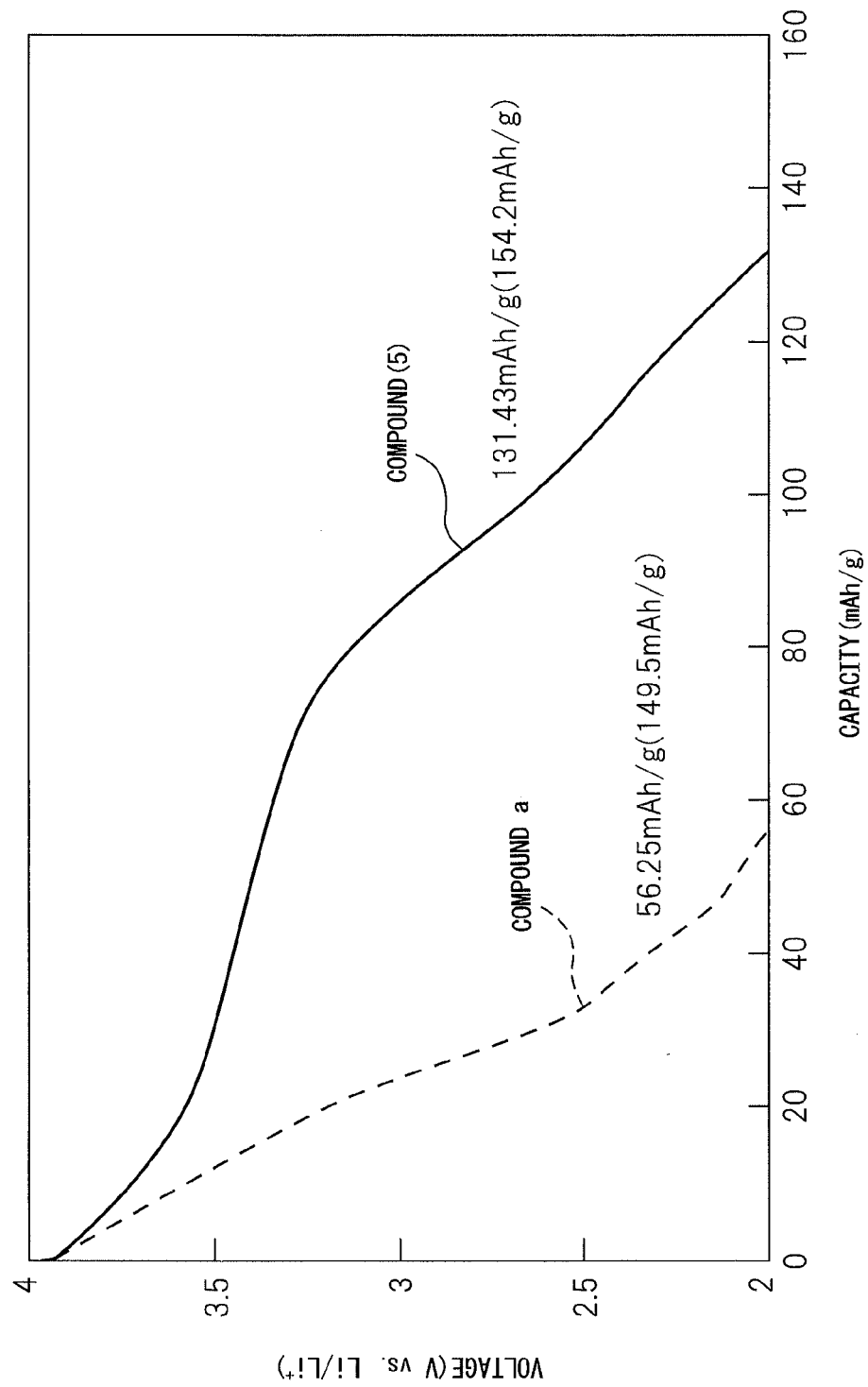
FIG. 6 is a graph showing discharge curves for the 10th cycle of coin-shaped lithium ion secondary batteries fabricated in Example 4-1 and Comparative Example 2.

The results of a charge-discharge test using the coin-shaped lithium ion secondary battery fabricated in Example 4-1 are shown in FIGS. 3 and 4. FIG. 3 represents the charge-discharge curves of the 10th cycle of testing (charge-discharge capacity value (mAh/g) and electron transfer number (n), while FIG. 4 represents the number of cycles (1 to 100 cycles) versus discharge capacity value (mAh/g) and electron transfer number (n). According to FIGS. 3 and 4, the discharge capacity value of the 10th cycle per weight of condensed polycyclic aromatic compound (5) was 131.9 (mAh/g). Since this discharge capacity value (131.9 (mAh/g)) is close to the theoretical capacity value (154.2 (mAh/g)), the condensed polycyclic aromatic compound (5) was confirmed to have the ability to transfer 3 electrons or more. The results of discharge tests using the coin-shaped lithium ion secondary batteries fabricated in Examples 4-1 to 4-3 and Comparative Example 2 are shown in FIGS. 5 and 6. FIGS. 5 and 6 represent the discharge curves (capacity (mAh/g) versus voltage (V)) of the 10th cycle of testing. As was previously described, the discharge capacity value of the 10th cycle per weight of condensed polycyclic aromatic compound (5) was 131.9 (mAh/g) (theoretical capacity value: 154.2 (mAh/g)), the discharge capacity value of the 10th cycle per weight of condensed polycyclic aromatic compound (11) was 119.0 (mAh/g) (theoretical capacity value: 143.9 (mAh/g)), the discharge capacity value of the 10th cycle per weight of condensed polycyclic aromatic compound (17) was 123.9 (mAh/g) (theoretical capacity value: 143.9 (mAh/g)), and the discharge capacity value of the 10th cycle per weight of compound b was 56.25 (mAh/g) (theoretical capacity value: 149.5 (mAh/g)). Similar to the condensed polycyclic aromatic compound (5), since the discharge capacity values of the condensed polycyclic aromatic compound (11) and the condensed polycyclic aromatic compound (17) were close to the theoretical capacity values of the condensed polycyclic aromatic compound (11) and the condensed polycyclic aromatic compound (17), the condensed polycyclic aromatic compound (11) and the condensed polycyclic aromatic compound (17) were confirmed have the ability to transfer 3 electrons or more. On the other hand, the discharge capacity value of compound b was far below the theoretical capacity value of compound b, and well-defined charge-discharge peaks were observed.

Example 5

Test of Adsorption to Conductive Assistant (Ketjen Black)

The condensed polycyclic aromatic compounds (5), (11) and (17) (2 mg) synthesized as previously described were respectively dissolved in 10 ml of chloroform. 1 ml aliquots were collected from each of the chloroform solution followed by the addition of Ketjen black (Ketjen Black International) to each solution to obtain samples A-1, A-2 and A-3 (Ketjen black added). Moreover, 1 ml aliquots were further collected from each of the chloroform solutions and nothing was added to these solutions. These were used as Samples B-1, B-2 and B-3 (Ketjen black not added). These six samples consisting of A-1, A-2, A-3 and B-1, B-2 and B-3 were irradiated with ultrasonic waves for 5 minutes and then allowed to stand for 30 minutes. The samples were filtered with a membrane filter having a pore diameter of 0.2 μm, supernatant was collected from each of the Samples A-1, A-2, A-3 and B-1, B-2 and B-3, and the visible-ultraviolet spectra of the supernatants of those samples were measured with a spectrophotometer (Hitachi).

Comparative Example 3

Test of Adsorption to Conductive Assistant (Ketjen Black)

A Sample C (Ketjen black added) and a Sample D (Ketjen black not added) were prepared and the visible-ultraviolet spectra thereof were measured using the exact same method as Example 5 with the exception of using the aforementioned compound b (2 mg) instead of the condensed polycyclic aromatic compounds (5), (11) and (17) synthesized in the manner previously described.

Results of Test of Adsorption to Conductive Assistant (Ketjen Black)

Figures 2, 7:
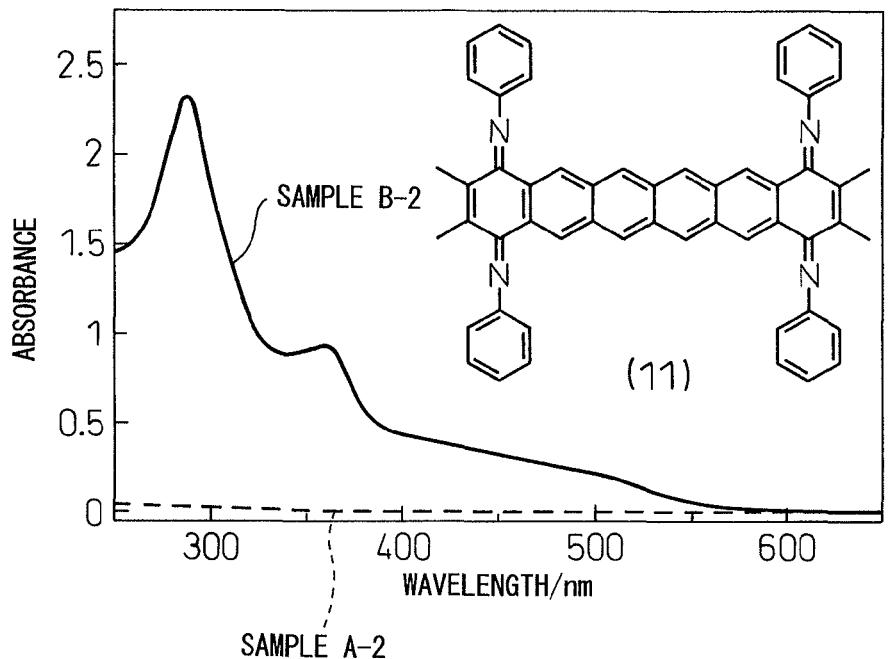
Figures 3, 7:
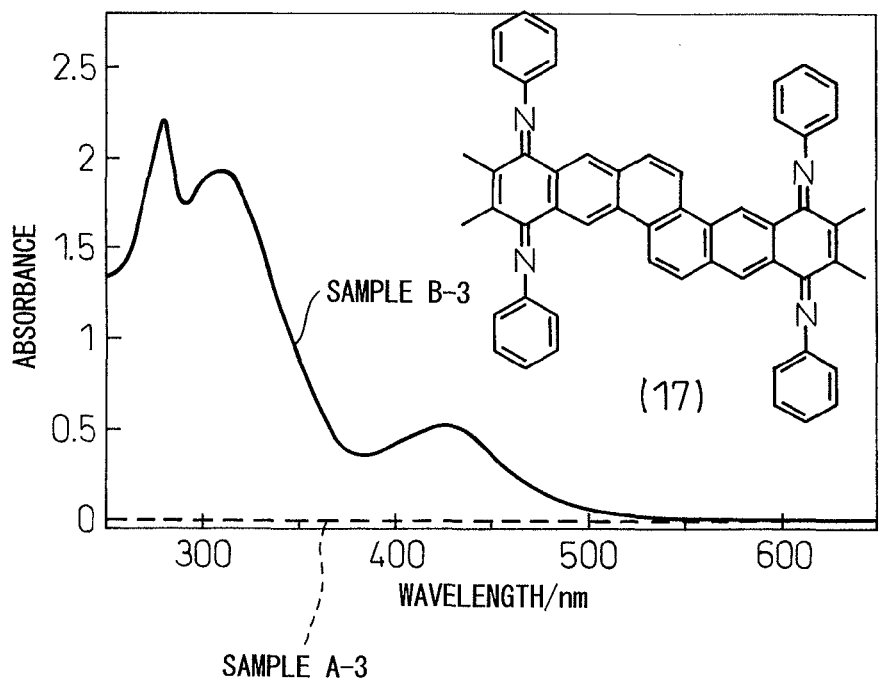

The results of the test of adsorption to conductive assistant (Ketjen black) are shown in FIGS. 7-1 to 7-3. As is clear from FIGS. 7-1 to 7-3, although Samples A-1 to A-3 to which Ketjen black was added demonstrated absorbance values of nearly 0 since they were transparent, Samples B-1 to B-3 to which Ketjen black was not added demonstrated absorbance spectra attributable to the condensed polycyclic aromatic compounds (5), (11) and (17) since they had a yellow color. On the basis of these results, the condensed polycyclic aromatic compounds (5), (11) and (17) were determined to be adsorbed to the Ketjen black. On the other hand, the Sample C to which Ketjen black was added and the Sample C to which Ketjen black was not added both demonstrated nearly the same yellow color. Although the absorbance of Sample C was lower than that of Sample D, they both demonstrated nearly the same absorbance spectra. On the basis of these results, the ability of compound b to adsorb to Ketjen black was determined to be inferior to the ability of condensed polycyclic aromatic compounds (5), (11) and (17) to adsorb to Ketjen black.

(Efficacy of Condensed Polycyclic Aromatic Compounds with Respect to Application to Lithium Ion Secondary Batteries)

As can be understood from the results of the tests of adsorption of condensed polycyclic aromatic compounds (5), (11) and (17) to a conductive assistant (Ketjen black) and the results of charge-discharge tests on lithium ion secondary batteries using the condensed polycyclic aromatic compounds (5), (11) and (17), the condensed polycyclic aromatic compound of the present invention can be present in the vicinity of a conductive assistant (Ketjen black) since it has affinity for a conductive assistant in the form of Ketjen black. Since the condensed polycyclic aromatic compound of the present invention can readily transfer electrons, a positive electrode provided with a positive electrode active material thereof can be used as a positive electrode for a lithium ion secondary battery.

The invention claimed is:
1. A condensed polycyclic aromatic compound having at least four imino groups in a molecule thereof which is represented by the following formula (1) or formula (2):

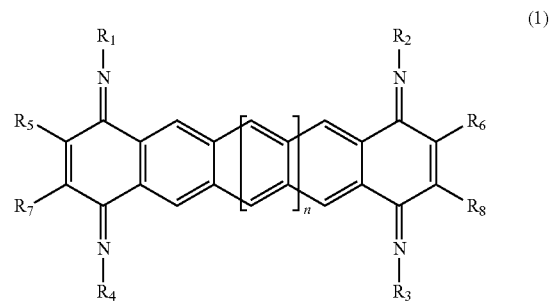

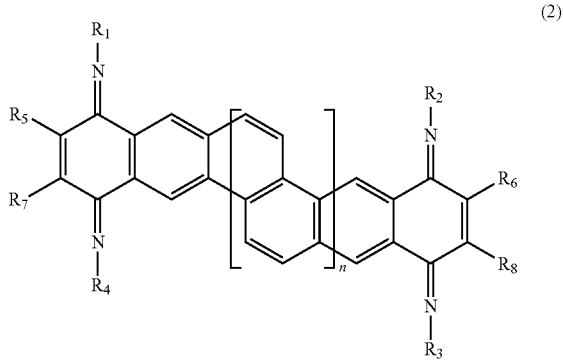

wherein, in formula (1), $R_1$, $R_2$, $R_3$, $R_4$, $R_5$, $R_6$, $R_7$ and $R_8$ respectively and independently represent a hydrogen atom, substituted or unsubstituted aliphatic hydrocarbon group or substituted or unsubstituted aromatic hydrocarbon group, n represents an integer of 1 to 10, and at least one of $R_1$, $R_2$, $R_3$ or $R_4$ is a substituted or unsubstituted aromatic group; and wherein, in formula (2), $R_1$, $R_2$, $R_3$, $R_4$, $R_5$, $R_6$, $R_7$ and $R_8$ respectively and independently represent a hydrogen atom, substituted or unsubstituted aliphatic hydrocarbon group or substituted or unsubstituted aromatic hydrocarbon group, n represents an integer of 1 to 10, and at least one of $R_1$, $R_2$, $R_3$ or $R_4$ is a substituted or unsubstituted aromatic group.

2. The condensed polycyclic aromatic compound according to claim 1, wherein the condensed polycyclic aromatic compound is represented by formula (1).

3. The condensed polycyclic aromatic compound according to claim 2, wherein neither $R_5$ and $R_7$ nor $R_6$ and $R_8$ of formula (1) join together to form a ring structure.

4. The condensed polycyclic aromatic compound according to claim 2, wherein, when the substituent $R_1$, $R_2$, $R_3$ or $R_4$ of formula (1) is a substituted or unsubstituted aliphatic group, the substituent is connected to the polycyclic aromatic compound via a carbon atom of the substituent.

5. The condensed polycyclic aromatic compound according to claim 1, wherein the condensed polycyclic aromatic compound is represented by formula (2).

6. The condensed polycyclic aromatic compound according to claim 5, wherein neither $R_5$ and $R_7$ nor $R_6$ and $R_8$ of formula (2) join together to form a ring structure.

7. The condensed polycyclic aromatic compound according to claim 5, wherein, when the substituent $R_1$, $R_2$, $R_3$ or $R_4$ of formula (2) is a substituted or unsubstituted aliphatic group, the substituent is connected to the polycyclic aromatic compound via a carbon atom of the substituent.

8. A production process of the condensed polycyclic aromatic compound according to claim 1, comprising reacting a compound having at least four oxo groups in a molecule thereof with an aniline-based compound in the presence of titanium tetrachloride and base.

9. A production process of the condensed polycyclic aromatic compound according to the formula (1) of claim 1, comprising reacting a compound represented by the following formula (3) with aniline in the presence of titanium tetrachloride and base:

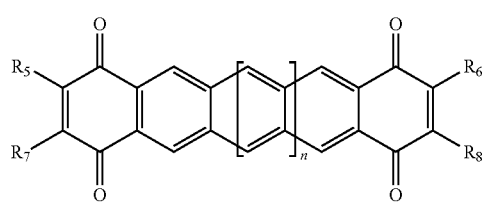

(3)

wherein, in formula (3), $R_5$, $R_6$, $R_7$ and $R_8$ are respectively the same as defined for $R_5$, $R_6$, $R_7$ and $R_8$ in general formula (1), and n represents an integer of 1 to 10.

10. A production process of the condensed polycyclic aromatic compound according to the formula (2) of claim 1, comprising reacting a compound represented by the following formula (4) with aniline in the presence of titanium tetrachloride and base:

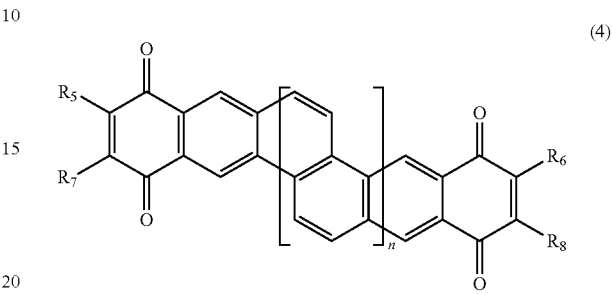

(4)

wherein, in formula (4), $R_5$, $R_6$, $R_7$ and $R_8$ are respectively the same as defined for $R_5$, $R_6$, $R_7$ and $R_8$ in general formula (2), and n represents an integer of 1 to 10.

11. A positive electrode active material for a lithium ion secondary battery, containing the condensed polycyclic aromatic compound according to claim 1.

12. A positive electrode active material for a lithium ion secondary battery, containing the condensed polycyclic aromatic compound according to the formula (1) of claim 1.

13. A positive electrode active material for a lithium ion secondary battery, containing the condensed polycyclic aromatic compound according to the formula (2) of claim 1.

14. A positive electrode for a lithium ion secondary battery, wherein the positive electrode active material according to claim 11 is provided at least on the surface of a current collector.

15. A positive electrode for a lithium ion secondary battery, wherein the positive electrode active material according to claim 12 is provided at least on the surface of a current collector.

16. A positive electrode for a lithium ion secondary battery, wherein the positive electrode active material according to claim 13 is provided at least on the surface of a current collector.

17. A lithium ion secondary battery comprising at least a positive electrode, a negative electrode and an electrolyte as constituents thereof, wherein the positive electrode is the positive electrode according to claim 14.

18. A lithium ion secondary battery comprising at least a positive electrode, a negative electrode and an electrolyte as constituents thereof, wherein the positive electrode is the positive electrode according to claim 15.

19. A lithium ion secondary battery comprising at least a positive electrode, a negative electrode and an electrolyte as constituents thereof, wherein the positive electrode is the positive electrode according to claim 16.

\* \* \* \* \*